US006296843B1

(12) United States Patent
Debinski

(10) Patent No.: US 6,296,843 B1
(45) Date of Patent: Oct. 2, 2001

(54) MUTAGENIZED IL 13-BASED CHIMERIC MOLECULES

(75) Inventor: Waldemar Debinski, Hershey, PA (US)

(73) Assignee: The Penn State Research Foundation

( * ) Notice: Subject to any disclaimer, the term of this patent is extended or adjusted under 35 U.S.C. 154(b) by 0 days.

(21) Appl. No.: 09/054,711

(22) Filed: Apr. 3, 1998

(51) Int. Cl.[7] .......................... A61K 45/00; A61K 39/00; A61K 38/00; C07K 14/00

(52) U.S. Cl. .................. 424/85.2; 424/185.1; 424/192.1; 530/351; 530/350; 514/2

(58) Field of Search .................................... 530/350, 351; 514/2; 424/85.2, 192.1, 185.1

(56) References Cited

U.S. PATENT DOCUMENTS

| | | |
|---|---|---|
| 4,671,958 | 6/1987 | Rodwell et al. . |
| 4,853,332 | 8/1989 | Mark et al. . |
| 5,458,878 | 10/1995 | Pastan et al. . |
| 5,614,191 | 3/1997 | Puri et al. . |

FOREIGN PATENT DOCUMENTS

| | | |
|---|---|---|
| WO 96/04306 * | 2/1996 | (WO) . |
| WO 96/29417 * | 9/1996 | (WO) . |

OTHER PUBLICATIONS

R.E. Callard et al., Eds. "The Cytokine FactsBook", Academic Press, New York, 1994. pp. 92–94.*

Bamborough et al., "Predictive modelling of the 3–D structure of itnerleukin–13," Prot. Eng., 7:1077–1082 (1994).

Bochner et al., "IL–13 Selectively Induces Vascular Cell Adhesion Molecule–1 Expression in Human Endothelial Cells," J. Immunol., 154:799–803 (1995).

Caput et al., "Cloning and Characterization of a Specific Interleukin (IL)–13 Binding Protein Structurally Related to the IL–5 Receptor α Chain," J. Biol. Chem. 271:16921–16926 (1996).

Chaudhary et al., "Pseudomonas exotoxin contains a specific sequence at the carboxyl terminus that is required for cytotoxicity," Proc. Natl. Acad. Sci., 87:308–312 (1990).

Chaudhary et al., "A Proper Amino Terminus of Diphtheria Toxin is Important for Cytotoxicity," Bioch. Biophys. Res. Comm., 180:545–551 (1991).

Chaudhary et al., "Mutagenesis of Pseudomonas Exotoxin in Indentification of Sequences Responsible for the Animal Toxicity," J. Biol. Chem., 265:16306–16310 (1995).

Debinski et al., "Substitution of Foreign Protein Sequences into a Chimeric Toxin Composed of Transforming Growth Factor α and Pseudomonas Exotoxin," Mol. Cell. Biol., 11:1751–1753 (1991).

Debinski et al., "Monoclonal Antibody C242–Pseudomonas Exotoxin A," J. Clin. Invest., 90:405–411 (1992).

Debinski et al., "A Wide Range of Human Cancers Express Interleukin 4(IL4) Receptors that can be Targeted with Chimeric Toxin Composed Of IL4 and Pseudomonas Exotoxin," J. Biol. Chem., 268:14065–14070 (1993).

Debinski et al., "Interleukin–4 Receptors Expressed on Tumor Cells May Serve as a Target for Anticancer Therapy Using Chimeric Pseudomonas Exotoxin," Int. J. Cancer 58:744–748 (1994).

Debinski et al., "Recombinant F(ab') C242–Pseudomonas Exotoxin, but not the Whole Antibody–based Immunotoxin, Causes Regression of a Human Colorectal Tumor Xenograft," Clin. Cancer Res., 1:1015–1022 (1994).

Debinski et al., "Human Glioma Cells Overexpress Receptors for Interleukin 13 and are Extremely Sensitive to a Novel Chimeric Protein Composed of Interleukin 13 and Pseudomonas Exotoxin," Clin. Cancer Res., 1:1253–1258 (1995).

Debinski, et al., "A Novel Chimeric Protein Composed of Interleukin 13 and Pseudomonas Exotoxin is Highly Cytotoxic to Human Carcinoma Cells Expressing Receptors for Interleukin 13 and Interleukin 14," J. Biol. Chem., 270:16775–16780 (1995).

Debinski et al., "Receptor for Interleukin (IL) 13 does not Interact with IL4 but Receptor for IL4 Interacts with IL13 on Human Glioma Cells," J. Biol. Chem. 271:22428–22433 (1996).

Debinski et al., Novel anti–brain tumor cytotoxins specific for cancer cells, Nature Biotechnology, 16:449–453 (1998).

Heimbrook, et al., "Transforming growth factor α–Pseudomonas exotoxin fusion protein prolongs survival of nude mice bearing tumor xenografts," Proc. Natl. Acad. Sci, 87:4697–4701 (1990).

Hilton et al., "Cloning and characterization of a binding subunit of the interleukin 13 receptor that is also a component of the interleukin 4 receptor," Proc. Natl. Acad. Sci, 93:497–501 (1996).

Husain et al., "Receptor for Interleukin 13 on AIDS–associated Kaposi's Sarcoma Cells Serves as a New Target for a Potent Pseudomonas Exotoxin–based Chimeric Toxin Protein," Clin. Cancer Res., 3:151–156 (1997).

(List continued on next page.)

*Primary Examiner*—Yvonne Eyler
*Assistant Examiner*—Janet L. Andres
(74) *Attorney, Agent, or Firm*—Akerman Senterfitt

(57) ABSTRACT

This invention provides mutagenized interleukin 13 molecules that show improved specificity for the restricted (IL4 independent) IL13 receptor and reduced cross-reactivity with the IL4/IL4 shared receptor. The mutagenized IL13 molecules include one or more mutations in a domain that interacts with the 140 kDa hIL4Rβ or the $hIL13R\alpha^1$ subunit. These mutagenized IL13 molecules provide effective targeting moieties in chimeric molecules (e.g. fusion proteins) that specifically deliver effector molecules (e.g. cytotoxins) to cells overexpressing IL13 receptors (e.g. cancer cells such as gliomas).

12 Claims, 6 Drawing Sheets

OTHER PUBLICATIONS

Idzerda, et al., "Human Interleukin 4 Receptor Confers Biological Responsiveness and Defines a Novel Receptor Superfamily," J. Exp. Med. 171:861–873 (1990).

Kreitman et al., "Purification and characterization of IL6–PE4E, a recombinant fusion of interleukin 6 with Pseudomonas exotoxin," Bioconjug. Chem., 4:581–585 (1993) [Abstract].

Kruse et al., "Two distinct functional sites of human interleukin 4 are identified by variants impaired in either receptor binding or receptor activation," EMBO J., 12:5121–5129 (1993).

Laske et al., "Tumor regression with regional distribution of the targeted toxin TF–CRM107 in patients with malignant brain tumors," Nature Medicine, 3:1362–1368 (1997).

McKenzie et al., "Interleukin 13, a T–cell–derived cytokine that regulates human monocyte and B–cell function," Proc. Natl. Acad. Sci 90:3735–3739 (1987).

Miloux et al., "Cloning of the human IL–13Rα1 chain and reconstitution with the IL–4Rα of a functional IL–4/IL–13 receptor complex," FEBS Letts., 401:163–166 (1997).

Minty et al., "Interleukin–13 is a new human lymphokine regulating inflammatory and immune responses," Nature, 362:248 (1993).

Murata et al., "Structure of IL–13 Receptor: Analysis of Subunit Composition in Cancer and Immune Cells," Biochem. Biophys. Res. Comm., 238:92–94 (1997).

Obiri, et al., "Receptor for Interleukin 13", J. Biol. Chem. 270:8797–8804 (1995).

Pastan, et al., "Recombinant Toxins as Novel Therapeutic Agents," Annu. Rev. Biochem., 61:331–354 (1992).

Phillips et al., "Transforming Growth Factor–α—Pseudomonas Exotoxin Fusion Protein ) TGF–α–PE38) Treatment of Subcutaneous and Intracranial Human Glioma and Medulloblastoma Xenografts in Athymic Mice," Cancer Res., 54:1008–1015 (1994).

Russell et al., "Interleukin–2 Receptor γ Chain: A Functional Component of the Interleukin–4 Receptor," Science, 262:1880–1883 (1993).

Schnyder et al., "Interleukin–4 (IL–4) and IL–13 Bind to a Shared Heterodimeric Complex on Endothelial Cells Mediating Vascular Cell Adhesion Molecule–1 Induction in the Absence of the Common γ Chain," Blood, 87:4286–4295 (1996).

Seetharam et al., "Increased Cytotoxic Activity of Pseudomonas Exotoxin and Two Chimeric Toxins Ending in KDEL," J. Biol. Chem. 266:17376–17381 (1991).

Siegall et al., "Functional Analysis of Domains II, Ib, and III of Pseudomonas Exotoxin," J. Biol. Chem., 264:14256–142610 (1989).

Sironi, "Regulation of Endothelial and Mesothelial Cell Function by Interleukin–13: Selective Induction of Vascular Cell Adhesion Molecule–1 and Amplification of Interleukin–6 Production," Blood 84:1913–1921 (1994).

Tony et al., "Design of human interleukin–4 antogonists inhibiting interleukin–4–dependent and inetrleukin–13–dependent responses in T–cells and B–cells with high efficiency," Eur. J. Biochem, 225:659–665 (1994).

Vita et al. "Characterization and Comparison of the Interleukin 13 Receptor with the Interleukin 4 Receptor on Several Cell Types," J. Biol. Chem, 270:3512–3517 (1995).

Wersäll et al., "Introtumoral infusion of the monoclonal antibody, mAb 425, against the epidermanl–growth–factor receptor in patients with advanced malignant glioma," Cancer Immunol. Immunother., 44:157–164 (1997).

Zurawski et al., "The Primary Binding Subunit of the Human Interleukin–4 Receptor is also a Component of the Interleukin–13 Receptor," J. Biol. Chem. 270:13869–13878 (1995).

* cited by examiner

SCHEME OF DISRUPTION OF hIL13/hIL4 RECEPTOR
BY MUTAGENIZED INTERLEUKIN 13

A - Human IL4 140 kDa Receptor Chain
B - Crosslinked 70 kDa/Cloned 50 kDa Human IL13
Binding Protein SCHEMATIC DRAWING OF A COMPACT CORE-BUNDLE
OF FOUR ANTI-PARALLEL α-HELICES CYTOKINES

| | |
|---|---|
| hIL13 | S P G P V P P S - - - - T A L R E L I E E L V N I ........ |
| mIL13 | A P G P V P R S V S L P L T L K E L I E E L S N I .... |
| hIL4 | H K C D - I T L Q E I I K T L N S L ... |
| mIL4 | H I H G C D K N H L R E I I G I L N E V .... |

SEQUENCE LISTING

```
<160> NUMBER OF SEQ ID NOS: 5

<210> SEQ ID NO 1
<211> LENGTH: 65
<212> TYPE: DNA
<213> ORGANISM: Artificial Sequence
<220> FEATURE:
<221> NAME/KEY: misc_feature
<223> OTHER INFORMATION: PCR primer for amplifying human IL-13 gene

<400> SEQUENCE: 1

aggagatata catatgtccc aggccctgtg cctccctcta cagccctcag gaagctcatt     60

gagga                                                                 65


<210> SEQ ID NO 2
<211> LENGTH: 38
<212> TYPE: DNA
<213> ORGANISM: Artificial Sequence
<220> FEATURE:
<221> NAME/KEY: misc_feature
<223> OTHER INFORMATION: PCR primer for amplifying human IL-13 gene

<400> SEQUENCE: 2

gtcgtgggtg gatcctcagt tgaaccgtcc ctcgcgaa                            38
```

-continued

<210> SEQ ID NO 3
<211> LENGTH: 132
<212> TYPE: PRT
<213> ORGANISM: homo sapiens

<400> SEQUENCE: 3

```
Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130
```

<210> SEQ ID NO 4
<211> LENGTH: 114
<212> TYPE: PRT
<213> ORGANISM: homo sapiens

<400> SEQUENCE: 4

```
Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn
```

<210> SEQ ID NO 5
<211> LENGTH: 114
<212> TYPE: PRT
<213> ORGANISM: homo sapiens

<400> SEQUENCE: 5

```
Ser Pro Gly Pro Val Pro Pro Ser Thr Ala Leu Arg Lys Leu Ile Glu
1               5                   10                  15

Glu Leu Val Asn Ile Thr Gln Asn Gln Lys Ala Pro Leu Cys Asn Gly
            20                  25                  30
```

-continued

```
Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn
```

MUTAGENIZED IL 13-BASED CHIMERIC MOLECULES

BACKGROUND OF THE INVENTION

In a chimeric molecule, two or more molecules that exist separately in their native state are joined together to form a single entity (molecule) having the desired functionality of all of its constituent molecules. Frequently, one of the constituent molecules of a chimeric molecule is a "targeting molecule". The targeting molecule is a molecule such as a ligand or an antibody that specifically binds to its corresponding target, for example a receptor on a cell surface. Thus, for example, where the targeting molecule is an antibody, the chimeric molecule will specifically bind (target) cells and tissues bearing the epitope to which the antibody is directed.

Another constituent of the chimeric molecule may be an "effector molecule." The effector molecule refers to a molecule that is to be specifically transported to the target to which the chimeric molecule is specifically directed. The effector molecule typically has a characteristic activity that is desired to be delivered to the target cell. Effector molecules include cytotoxins, labels, radionuclides, other ligands, antibodies, drugs, prodrugs, liposomes, and the like.

In particular, where the effector component is a cytotoxin, the chimeric molecule may act as a potent cell-killing agent specifically targeting the cytotoxin to cells bearing a particular target molecule. For example, chimeric fusion proteins which include interleukin 4 (IL4) or transforming growth factor (TGFα) fused to Pseudomonas exotoxin (PE), interleukin 2 (IL2) fused to Diphtheria toxin (DT) have been shown to specifically target and kill cancer cells (Pastan et al., *Ann. Rev. Biochem.*, 61: 331–354 (1992)).

The targeting moiety of these chimeric cytotoxins is often selected to pacifically target and bind to growth factor receptors, particularly those receptors that are overexpressed on cancer cells as compared to normal cells (e.g., Debinski et al. (1993) *J. Biol. Chem.*, 268: 14065–14070, Phillips et al. (1994) *Cancer Res.*, 54: 1008–1015, Debinski et al. (1994) *Int. J. Cancer*, 58: 744–748). However, even where the target receptor is overexpressed on cancer cells there is typically a significant level of receptor expression on normal cells as well. Therefore, even though one can obtain a therapeutic window for the cytotoxins, toxicities related to the presence of growth factor receptors on normal cells are dose-limiting for their administration (Phillips et al. (1994) *Cancer Res.*, 54: 1008–1015, Debinski et al. (1994) *Int. J. Cancer*, 58: 744–748). It is thus desirable to identify targets or targeting ligands that show provide increased specificity for cancer cells as compared to normal cells and thereby improve the dosage levels that can be administered with diminished or no toxic side-effects.

SUMMARY OF THE INVENTION

This invention provides novel targeting ligands (specific binding moieties) that have increased specificity for cancer cells as compared to normal cells and therefore extremely effective for specifically delivering effector molecules to various neoplasias. The targeting ligands are mutagenized IL13 molecules having one or more mutations in the domain that interacts with the hIL4 receptor subunit designated the 140 kDa $hIL4R_\beta$ subunit.

Particularly preferred mutagenized IL13 molecules (specific binding moieties) of this invention are mutagenized human IL13 molecules. These molecules can be mutated at one or more of a variety of residues including at residues 12, 13, 14, 65, 66, 67, 68, 69, 70, 109, or 112. In one particular embodiment, residue 13 is a basic amino acid. Other preferred mutagenized IL13 molecules include lysine or arginine at residue 13 and/or aspartic acid at residue 66 and/or aspartic acid at residue 69 and or aspartic acid at residue 109 or 112. When a native human IL13 is mutated these mutations can include hIL13.E13R, hIL13.R66D, hIL13.S69D, hIL13.E13K, hIL13.R109D, and hIL13.R112D. Preferred double mutations include hIL13.E13K/R66D or hIL13.E13K/S69D. The specific binding moieties (mutagenized IL13) can be attached to and therefore comprise an effector molecule as described herein.

In one embodiment, any of the mutagenized IL13 molecules described herein is a component of a chimeric molecule having the formula:

$$R^1—(L)_j—(R^2)_n$$

in which $R^1$ is the mutagenized human interleukin 13, j and n are independently 0 or 1; $R^2$ is an effector molecule; and L is an optional linker. The effector molecule can be virtually any molecule that can be attached to the mutagenized IL 13. Effector molecules include, but are not limited to cytotoxins, labels, antibodies, liposomes, lipids, DNA or RNA nucleic acids, DNA or RNA vector, recombinant viruses, chemotherapeutics, anti-cancer antibiotics, photosensitizers, and the like. Particularly preferred cytotoxins include a Pseudomonas exotoxin or a Diphtheria toxin. The Pseudomonas exotoxin can be modified such that it substantially lacks domain Ia, and most preferred Pseudomonas exotoxins include PE38QQR and PE4E. It will be appreciated that the effector molecule can be attached to either the amino terminus, the carboxyl terminus or to an internal residue of the mutagenized IL13 molecule although terminal attachment is preferred.

Preferred cytotoxic chimeric molecules are fuision proteins and include any of the mutagenized IL13 molecules described herein fused to the cytotoxin. Particularly preferred cytotoxins include any of the above mutagenized IL13 molecules fused to a Pseudomonas exotoxin (e.g., hIL13.E13K-PE38QQR, hIL13.E13K-PE4E, etc.). Particularly preferred cytotoxic molecules include, but are not limited to hIL13.E13K-PE38QQR, hIL13.E13K-PE4E, hIL13.R66D-PE38QQR, hIL13.R66D-PE4E, hIL13.S69D-PE38QQR, hIL13.S69D-PE4E, hIL13.R109D-PE38QQR, hIL13.R112D-PE38QQR, hIL13.R109D-PE4E, hIL13.R112D-PE4E hIL13.E13K/R109D-PE38QQR, hIL13.E13K/R112D-PE38QQR, hIL13.E13K/R66D-PE4E, hIL13.E13K/RS69D-PE4E, DT390-hIL13.E13K, DT390-hIL13.R66D, DT390-hIL13.S69D, DT390-hIL13.R109D, DT390-hIL13.R112D, DT390-hIL13.E13K/R109D, and DT390-hIL13.E13K/R112D.

In another embodiment, this invention provides methods of delivering an effector molecule to a cell bearing an interleukin 13 receptor (IL13R). The methods involve contacting the cell with a chimeric molecule comprising the effector molecule attached to any of the mutagenized interleukin 13 (IL13) molecules described herein. The methods can involve any of the chimeric molecules described herein.

Where the effector molecule is a cytotoxin, this invention provides methods of killing a cell or inhibiting the growth (and/or proliferation) of a cell expressing an IL13 receptor (IL13R). Again, these methods involve contacting the cell any of the mutagenized IL13-cytotoxin chimeric molecules described herein. In a preferred embodiment, the cell is a neoplastic cell (e.g. a glioma).

The cytotoxic chimeric molecules described herein can be used as components of a pharmacological composition. In this embodiment, the composition comprises any one or more of the cytotoxic chimeric molecules of this invention and a pharmacologically acceptable excipient, The mutagenized IL13 can also be attached to a detectable label. The chimeric label can be used to detect and/or localize and/or quantify a cell or cells expressing an IL13 receptor. The label when administered to a subject will localize at the site(s) of cells expressing or overexpressing IL13 receptors and detection of the label provides an indication of the presence, absence, quantity or location of such cells. Similarly ex vivo detection can be accomplished e.g. using a biological sample taken from the subject.

This invention also provides kits for the detection of cells expressing IL13 receptors or for inhibiting the growth and/or proliferation of such cells. The kits preferably include one or more containers containing a mutagenized IL13 of this invention. The mutagenized IL13 can be attached to either label (e.g. for detection of an IL13R bearing cell) or a cytotoxin (e.g. for inhibiting the growth of an IL13R bearing cell). Any of the cytotoxic or label (or other) chimeric molecules of this invention can be included in the kit.

DEFINITIONS

The term "specifically binds", as used herein, when referring to a protein or polypeptide, or receptor refers to a binding reaction which is determinative of the presence of the protein or polypeptide or receptor in a heterogeneous population of proteins and other biologics. Thus, under designated conditions (e.g. immunoassay conditions in the case of an antibody), the specified ligand or antibody binds to its particular "target" (e.g an IL13 specifically binds to an IL13 receptor) and does not bind in a significant amount to other proteins present in the sample or to other proteins to which the ligand or antibody may come in contact in an organism.

The hIL4 receptor subunit designated the 140 kDA $hIL4R_\beta$ subunit refers to a polypeptide that is common to a shared IL13/IL4 receptor and all other IL4 receptors on "normal" (non-neoplastic cells) such as HUVEC (endothelial cells) (see, e.g., Idzerda et al. (1990) *J. Exp. Med.*, 171: 861–873).

The phrase "a domain that interacts (or specifically interacts) with the hIL13/IL4 receptor subunit designated the 140 kDA $hIL4R_\beta$ subunit", as used herein, refers to a domain of a polypeptide (e.g. IL13) disruption of which reduces or eliminates binding of an IL13 to the IL13/IL4 receptor or that reduces or eliminates effector activity (e.g. cytotoxic activity) of a chimeric molecule having the disrupted IL13 molecule on a cell or cells that express the 140 kDa hIL4Rβ, subunit (e.g., HUVEC endothelial cells). Alteration of one or more amino acids in the domain preferably diminishes or eliminates interaction with cells expressing the 140 kDA $hIL4R_\beta$ subunit but shows improvement in the interaction of the IL13 or IL13 chimeric molecule on cells over-expressing restrictive IL4R-independent IL13 binding sites (e.g., on gliomas).

A mutation in a polypeptide refers to the substitution of an amino acid at a particular position in a polypeptide with a different amino acid at that position. Thus, for example, the mutation hIL13.E13K indicates that the native amino acid at position 13 in IL13 (glutamic acid, E) is replaced with lysine (K). The "mutation" does not require an actual removal and substitution of the amino acid(s) in question. The protein can be created de novo with the "replacement" amino acid in the position(s) of the desired mutation(s) so the net result is equivalent to the replacement of the amino acid in question.

A "mutagenized IL13 " or "mutagenized hIL13" refers to an IL13 in which one or more of the amino acids differ from the corresponding amino acids in the native form of the IL13. Thus, for example, where a native human IL13 has a glutamic acid at position 13, a mutagenized human IL13 can have an amino acid other than glutamic acid at position 13 (e.g., glutamic acid is substituted with lysine). It will appreciated that mutagenized IL13 molecules of this invention include mutagenized IL13 molecules of other mammalian species (e.g., rat, murine, porcine, largomorph, non-human primates, bovine, canus, and the like) and this invention contemplates the use of chimeric molecules in veterinary as well as human medical conditions.

A chimeric molecule, as used herein refers to a molecule in which, two or more molecules that exist separately in their native state are joined together to form a single entity (molecule) having the desired functionality of all of its constituent molecules. Preferred chimeric molecules of this invention involve one or more IL13 (more preferably a mutagenized human IL13) joined to one or more effector molecules. The mutagenized IL13 acts as a targeting molecule preferably binding the chimeric molecule to cells expressing or overexpressing a restrictive IL4R-independent IL13 receptor (IL13R).

A fusion protein as used herein is a chimeric molecule in which the components making up the chimeric molecule are polypeptides and the polypeptides are joined directly (or through a peptide linkage) via peptide bonds. The fusion protein thus forms a continuous single polypeptide having domains corresponding to the different (e.g., targeting and effector) components.

A "specific binding moiety" or a "targeting moiety" refers to a molecule (e.g., a polypeptide) that specifically binds to a particular target. Thus, for example, an interleukin-13 (IL13) is a specific binding moiety that specifically binds to an IL13 receptor (although it will be recognized that where the IL13 receptor shares a component with an IL4 receptor) the specific binding moiety may cross-react with the IL4 receptor. Nevertheless the binding moiety is still regarded as specific because its interaction is specific to these two components and it does not generally bind to any protein found in the organism or biological sample. Preferred specific binding moieties of this invention preferentially bind to the restrictive IL4R-independent tumor associated IL13 receptor rather than the IL4 receptor and typically show an avidity and/or specificity for an IL13 receptor at least 1.5-fold, preferably at least 2-fold, more preferably at least 5-fold, and most preferably at least 10-fold or even at least 100-fold greater than its affinity and/or specificity for an IL4 receptor.

An "effector molecule" as used herein, refers to a molecule that it is desired to deliver to a particular target (e.g., to a target cell). The effector molecule preferably has a characteristic activity that is desired to be delivered to the target cell. Effector molecules include cytotoxins, labels, radionuclides, other ligands, antibodies, drugs, prodrugs, liposomes, lipids, recombinant viruses, chemotherapeutics, anti-cancer antibiotics, photosensitizers, and the like. It will be appreciated that some effectors once delivered to the cell are preferentially internalized while others (such as labels) need not be internalized. However many effectors (e.g., PE, or DT cytotoxins) are more effective on internalization.

The term "delivering an effector molecule to a cell" refers to preferentially binding such that when an organism is systemically treated with a chimeric molecule comprising a mutagenized IL13 of this invention, or when a cell culture is treated with a chimeric molecule comprising a mutagenized IL13 of this invention, the chimeric molecule preferentially accumulates adjacent to or on the target cell or is preferentially internalized by the cell as compared to cells lacking or having a lower concentration of the target to which the mutagenized IL13 is directed (e.g. the IL13 receptor).

The term "inhibiting the growth of a cell" refers to inhibition of growth and/or proliferation of a cell or cells. Such inhibition may involve killing of one or more cells. Methods of assaying cell growth and/or proliferation are well known to those of skill in the art.

The terms "isolated" or "substantially purified" or "isolated" when referring to a protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques. The term "purifying" when used in reference to a protein or a receptor refers to rendering the protein or receptor in such an isolated or substantially purified state.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides. The term also include nucleotides linked by peptide linkages as in "peptide" nucleic acids.

DETAILED DESCRIPTION

This invention provides ligands that are highly specific to the IL13 receptor and, when incorporated into chimeric molecules (e.g., chimeric fusion proteins) are capable of specifically directing the chimeric molecules to cells expressing IL13 receptors. Since IL13 receptor targets are characteristically overexpressed on cancer cells, the targeting agents of this invention are particularly useful for specifically directing agents to those cancer cells (e.g., gliomas). In a preferred embodiment, the ligands are mutagenized IL13 molecules, in particular, IL13 molecules containing one or more mutations in a domain that interacts with the hIL13/hIL4 receptor subunit designated the 140 kDA hIL4$R_\beta$ subunit.

The target IL13 receptors are growth factor receptors that show a number of similarities to the IL4 receptors. Studies of the similarities and differences between the IL13 receptor (IL13R) and the IL4 receptor (IL4R) suggest that IL13 binds to the IL4 receptor (as well as to the IL13 receptor) and that IL13 binding to the IL4 receptor is fully competed for by IL4 (Zurawski et al. (1995) *J. Biol. Chem.*, 270: 13869–13878, Vita et al. (1995) *J. Biol. Chem.*, 270: 3512–3517, and Tony et al. (1994) *Eur. J. Biochem.*, 225: 659–665)).

Figure 1:
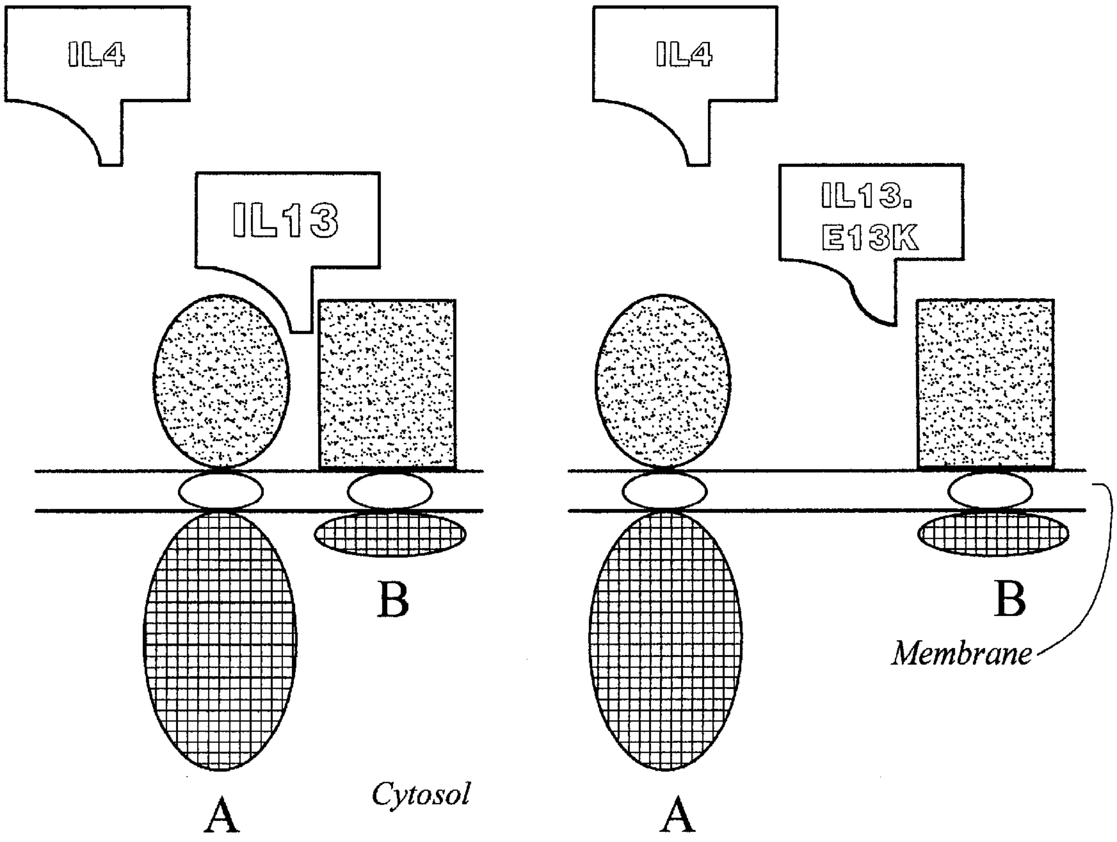
FIG. 1 shows a schematic model of hIL13/hIL4R and the effect of mutagenized interleukin 13 on it.
Figures 2, 3:
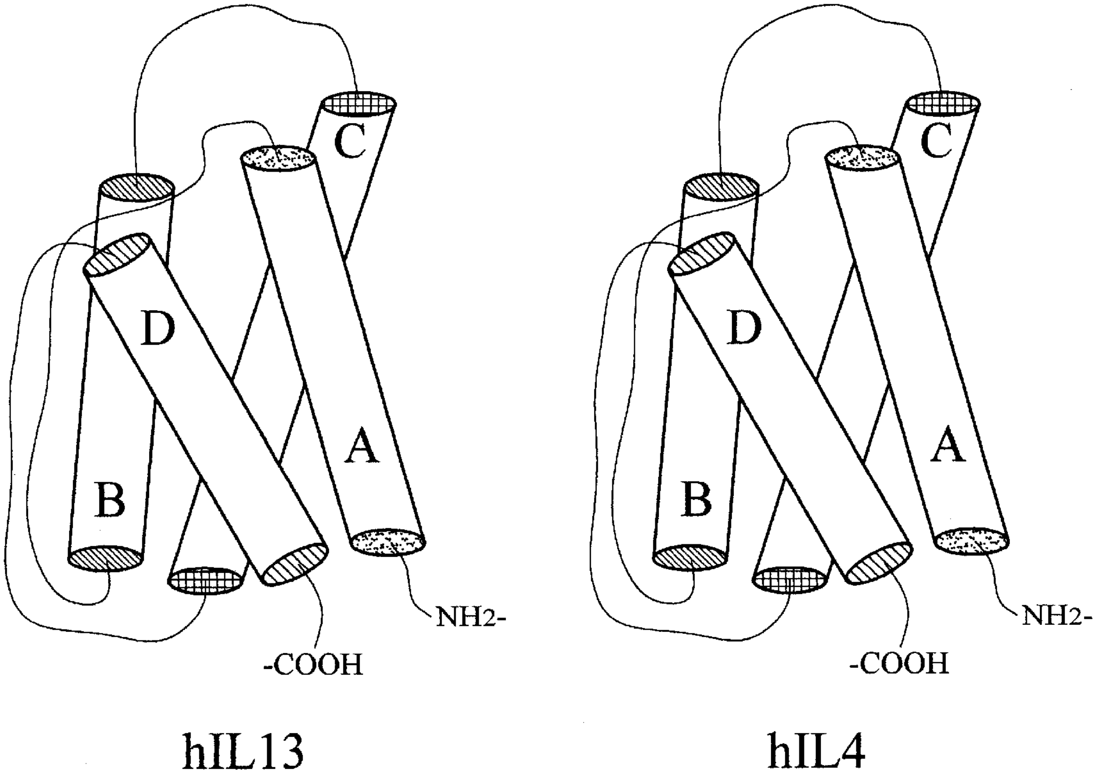
FIG. 2 shows a schematic drawing of interleukin 13 and interleukin 4.
FIG. 3 shows the N-termini of both human and murine interleukin 13 and interleukin 4 ending at the first α-helix, α-helix A. Amino acids which form the α-helix A are underlined. The conserved residue of glutamic acid is typed in boldface font.

A recently proposed model for the hunan IL13 receptor suggests that it is heterodimeric and comprises an hIL13 binding protein (Debinski et al. (1995) *J. Biol. Chem.*, 270: 16775–16780), Obiri et al. (1995) *J. Biol. Chem.* 270: 8797–8804, Caput et al. (1996) *J Biol. Chem.* 271: 16921–16926; Hilton et al. (1996) *Proc. Natl. Acad. Sci., USA*, 93: 497–501) and a 140 kDa hIL4$R_\beta$ (Obiri et al. (1996) *Clin. Cancer Res.* 2: 1743–1749) (FIG. 1). The latter is a subunit shared with the hIL4 receptor (Debinski et al. (1996) *J. Biol. Chem.*, 271: 22428–22433, Zurawski et al. (1995) *J. Biol. Chem.*, 270: 13869–13878, Vita et al. (1995) *J. Biol. Chem.*, 270: 3512–3517, and Tony et al. (1994) *Eur. J. Biochem.*, 225: 659–665, Hilton et al. (1996) *Proc. Natl. Acad. Sci. USA*, 93: 497–50 1). Thus, human interleukin-13 (hIL13) may contain at least two receptor interaction sites (domains): (i) one which recognizes the 140 kDa hIL4$R_\beta$ subunit, and (ii) another site which interacts with its proper binding proteins (Obiri et al. (1995) *J. Biol. Chem.* 270: 8797–8804, Caput et al. (1996) *J Biol. Chem.* 271: 16921–16926; Hilton et al. (1996) *Proc. Natl. Acad. Sci., USA*, 93: 497–501). These putative sites are proposed here based on structural homology to hIL4 and the belief that hIL13 exists as a compact core-bundle of the four anti-parallel a-helices cytokine (FIG. 2).

A predictive model of hIL13 is described by Bamborough et al. (1994) *Prot. Eng.*, 7: 1077–1082. This model is analogous to the model of hIL4 which proposes that IL4 binds the 140 kDa hIL4$R_\beta$ through one site and the $\gamma_c$ , subunit through another site which produces heterodimeric high affinity hIL4R (Russell et al. (1993) *Science*, 262: 1880–1883). A mutation of glutamic acid at position 9 to lysine in hIL4 (hIL4.E9K) severely impairs binding of hIL4 to the 140 kDa $hIL4R_\beta$ (Kruse et al. (1993) *EMBO J.* 12: 5121–5129) (FIG. 3).

Recently, it was demonstrated that human (h) gliomas express large number of receptors (R) for interleukin 13 (IL13) (Debinski et al. (1995) *Clin. Cancer Res.* 1: 12531–1258). It was also shown that both IL4 and an antagonist of hIL4, hIL4.Y124D, which binds the 140 kDa hIL4R β-chain protein and block the effects of hIL13 and hIL4 on normal cells, did not block the binding and internalization of IL13 in glioma cells unlike on normal cells and some adenocarcinomas (Debinski et al. (1995) *Clin. Cancer Res.* 1: 1253–1258; Debinski et al. (1996) *J. Biol. Chem.* 271: 22428–224; Debinski et al. (1995) *J. Biol. Chem. 270; 16775–16780*). These and other findings demonstratc the existence of hIL13 receptors (e.g., on cancers) that do not interact with IL4 and presumably do not involve the 140 kDa hIL4R β-chain (hIL4Rβ)

This was demonstrated by the observation that the use of hIL4 and hIL4.Y124D in conjunction with IL13R directed chimeric molecules enhanced the specificity of these molecules to cells bearing the IL13 receptor.

It is demonstrated herein that a similar effect to that exhibited by hIL4 and hIL4.Y124D can be obtained by mutagenizing IL13 itself and using the mutagenized IL13 as a targeting moiety in a chimeric molecule. In one embodiment, cytotoxins are described herein in which the targeting moiety (IL13) is mutagenized by changing glutamic acid at position 13 to lysine (producing hIL13.E13K) and the toxic effector molecule is a Pseudomonas exotoxin A (PE) derivative (e.g., PE38QQR, or PE4E).

It is also taught herein that by altering a putative binding site of IL13 which interacts with the 140 kDa IL4 receptor β-chain, one can alter interaction of the cytotoxins (or other IL13R-directed chimeric molecules) with the IL13R and IL4R common elements that are predominantly expressed in normal tissues. Indeed, it is demonstrated herein that, for example, hIL13.E13K-PE4E is less active on normal cells, such as endothelial cells, which do express elements common to both hIL4 and hIL13R. Unexpectedly, the action of hIL13.E13K-PE4E was considerably more potent on human glioma cells when compared with that containing the wild-type hIL13. Toxicities of the hIL13.E13K-based cytotoxins in vivo are also several times lower when compared with chimeric cytotoxins utilizing unmutagenized hIL13 as a targeting moiety. Thus, it is demonstrated herein that a mutation in the domain of IL13 that interacts with the hIL4 receptor subunit designated the 140 kDa $hIL4R_\beta$ subunit (e.g., a mutation at IL13 residue 13) makes a chimeric cytotoxin less active on normal cells and, surprisingly, much more active on glioma cells. The increase in an overall specific cytotoxic activity can be as high as 100-fold. Thus, hIL13 is amenable to engineering which leads to a much more discriminate recognition of the hIL13R that is expressed on cancer cells from the one present on normal cells.

As explained below, in a preferred embodiment the mutagenized IL13 can be provided as a component of a chimeric molecule. Alternatively, the mutagenized IL13 may be provided alone to bind to and thereby specifically block the IL13 receptor.

I. Uses of Chimeric Molecules Targeted to the IL13 Receptor

Using the mutagenized IL13 molecules, this invention provides in one embodiment, methods for specifically delivering an effector molecule to a cell bearing an IL13 receptor (e.g., a tumor cell such as a glioma). These methods utilize chimeric molecules comprising a mutagenized IL13 (targeting molecule) attached to an effector molecule. The chimeric molecules of this invention specifically target tumor cells (especially glioma cells) while providing reduced binding to non-target cells as compared to other targeted chimeric molecules known in the art.

This allows specific delivery of any of a number of effector molecules to the target cell(s). Where the effector molecule is a cytotoxin, this invention provides for methods and compositions for impairing the growth and/or proliferation of cells (e.g., free cells or cells in tumors). The chimeric cytotoxin is administered to an organism containing IL13 receptor-bearing cells (e.g., cancer cells) which are then contacted by the chimeric molecule. The mutagenized IL13 component of the chimeric molecule specifically binds to the overexpressed IL13 receptors on the cells. Once bound to the IL13 receptor on the cell surface, the cytotoxic effector molecule mediates internalization into the cell where the cytotoxin inhibits cellular growth or kills the cell. The cytotoxin may be a native or modified cytotoxin such as Pseudomonas exotoxin (PE), Diphtheria toxin (DT), ricin, abrin, and the like.

In another embodiment, the chimeric molecules of this invention can provide compositions and methods for detecting the presence or absence of tumor cells. These methods involve providing a chimeric molecule comprising an effector molecule, that is a detectable label attached to a mutagenized IL13. The mutagenized IL13 specifically binds the chimeric molecule to IL13R bearing target cells (e.g., tumor cells) which are then marked by their association with the detectable label. Subsequent detection of the cell-associated label indicates the presence of the target cell.

In yet another embodiment, the effector molecule may be another specific binding moiety such as an antibody, a growth factor, or a ligand. The chimeric molecule will then act as a highly specific bifunctional linker. This linker may act to bind and enhance the interaction between cells or cellular components to which the fusion protein binds. Thus, for example, where the chimeric molecule comprises a mutagenized IL13 of this invention attached to an antibody or antibody fragment (e.g. an Fv fragment of an antibody), the mutagenized IL13 specifically binds target cells (e.g., cancer cells), while the effector component binds receptors (e.g., IL-2 or IL-4 receptors) on the surface of immune cells. The chimeric molecule may thus act to enhance and direct an immune response toward target cancer cells. Alternatively, the mutagenized IL13 can be attached to a bacterial superantigen such as Staphylococcal Enterotoxin A and B (SEA and SEB), or other superantigens and can thereby activate immune cells which will target a response to the cells (e.g., glioma cells) bearing the chimeric molecule.

In still yet another embodiment the effector molecule may be a pharmacological agent (e.g. a drug) or a vehicle containing a pharmacological agent. Thus the mutagenized IL13s of this invention may be conjugated to a drug such as vinblastine, doxorubicin, genistein (a tyrosine kinase inhibitor), an antisense molecule, ribozymes, and other pharmacological agents known to those of skill in the art, thereby specifically targeting the pharmacological agent to target cells over expressing IL13 receptors.

Alternatively, the mutagenized IL13 may be bound to a vehicle containing the therapeutic composition. Such vehicles include, but are not limited to liposomes, lipids, micelles, various synthetic beads, and the like.

One of skill in the art will appreciate that the chimeric molecules of the present invention may include mutagenized IL13 molecules bound to a single effector or conversely, multiple effector molecules bound to a single mutagenized IL13 molecule. Thus, one embodiment one effector may be bound to the mutagenized IL13 amino terminus while another effector is bound to the mutagenized IL13 carboxyl terminus. The two effectors can be the same or different.

In still other embodiment, the chimeric molecules may include both multiple mutagenized IL13 molecules and multiple effector molecules. Thus, for example, this invention provides for "dual targeted" cytotoxic chimeric molecules in which the mutagenized IL13 is attached to a cytotoxic molecule and another molecule (e.g. an antibody, or another ligand) is attached to the other terminus of the toxin. Such a dual-targeted cytotoxin might comprise a mutagenized IL13 substituted for domain Ia at the amino terminus of a PE and anti-TAC(Fv) inserted in domain III, between amino acid 604 and 609. Other antibodies may also be suitable.

II. Mutagenized Interleukin 13 (IL13)

It was a discovery of this invention that mutagenized IL13 provides a ligand having improved specificity for cells expressing a restrictive (IL4 receptor independent) IL13 receptor. Moreover, because the mutagenized IL13 does not significantly bind to the 140 kDa hIL4$R_\beta$ subunit that is shared by both the IL13 receptor (on non-neoplastic cells) and the IL4 receptor, the mutagenized IL13 shows reduced binding to normal cells expressing the IL13/IL4 receptor. Particularly preferred mutagenized IL13 ligands of this invention have one or more mutations in the domain that interacts with 140 kDa hIL4$R_\beta$ subunit as described below.

Native interleukin-13 (IL13) is a pleiotropic cytokine that is recognized to share many of the properties of IL4. IL13 has approximately 30% sequence identity with IL-4 and exhibits IL4-like activities on monocytes/macrophages and human B cells (Minty et al., *Nature*, 362: 248 (1993), McKenzie et al. *Proc. Natl. Acad. Sci. USA*, 90: 3735 (1987)).

The nucleic acid and amino acid sequences of IL13 are well characterized (see, e.g. SWISS-PROT: P35225, McKenzie et al. (1993) *Proc. Natl. Acad. Sci. USA*, 90: 3735–3739) and either the polypeptide or nucleic acid sequence information can be used for the production of mutagenized IL13 as described below and in Example 1.

A) Preferred Mutagenized IL13 molecules.

In a preferred embodiment, the mutagenized IL13 molecules of this invention show diminished interaction with the shared IL13/IL4 receptor and the same or improved interaction (e.g. binding or receptor mediated activity) with the restrictive (IL4R independent) IL13 receptor. As explained above, this is accomplished by mutagenizing the IL13 to reduce or eliminate interaction of the mutagenized IL13 (or chimeric molecule) with the 140 kDa IL4$R_\beta$ subunit. This is preferably accomplished by introducing mutations in the IL13 domain that interacts with the 140 kDa IL4$R_\beta$.

Preferred mutations are thus located at in α-helix A and C. Preferred mutagenized IL13 molecules include mutations of one or more of residue 13 and/or residue 66 and/or residue 69 and/or residue or residues 12, 14, 65, 67, 68, 70, and 76. Particularly preferred mutations include one or more of the following mutations: mutation of residue 13 to lysine or arginine, mutation of residue 66 to aspartic acid, mutation of residue 69 to aspartic acid or mutation of residue 109 or 112 to aspartic acid.

Another mutagenizing strategy is to identify hIL13 mutants that are deprived of interaction with their proper binding protein (e.g., hIL13Rα[1]) which is the other subunit of the shared IL13/IL4 receptor (FIG. 1 and Miloux et al. (1997) *FEBS Letts*., 401: 163–166). This is consistent with IL13 having two receptor recognition sites. Such mutations can include hIL13.R109D, hIL13.R112D, hIL13.F113D, etc. Other suitable mutagenized IL13 molecules can be routinely identified using the methods described below.

B) Screening for Mutagenized IL13 Molecules.

As indicated above, preferred mutagenized IL13 molecules have mutations that diminish or eliminate interaction with the human IL4 receptor subunit designated the 140 kDa hIL$R_\beta$ subunit, while not diminishing, and even increasing, their specificity and avidity for a restrictive, cancer-asssociated IL13 receptor, especially for an IL13 receptor that does not include the 140 kDa hIL$R_\beta$. Identifying such mutagenized IL13 molecules generally involves first producing one or more mutagenized IL13 molecules and then screening the mutagenized IL13 molecules to identify those that do not interact with the shared IL4/IL13 receptor, but still bind to a restrictive (IL-4 receptor independent) IL13 receptor.

i) Mutagenizing IL13

Mutagenized IL13 molecules for use in this invention can routinely be produced and screened. Numerous means of mutagenizing polypeptides are well known to those of skill in the art. Since the amino acid sequence of native IL13 is fully known, mutagenized IL13 molecules can be chemically synthesized or recombinantly expressed.

Mutated IL13 polypeptides of this invention may be synthesized using standard chemical peptide synthesis techniques. Some IL13 muteins can be synthesized as a single polypeptide. Chemical synthesis may, however, be facilitated by separately synthesizing subsequences and then fusing the subsequences by condensation of the amino terminus of one molecule with the carboxyl terminus of the other molecule thereby forming a peptide bond. Techniques for solid phase synthesis of polypeptides are well known to those of skill in the art (see, e.g., Barany and Merrifield, *Solid-Phase Peptide Synthesis*; pp. 3–284 in *The Peptides: Analysis, Synthesis, Biology*. Vol. 2*: Special Methods in Peptide Synthesis, Part A*., Merrifield, et al. *J. Am. Chem. Soc*., 85: 2149–2156 (1963), and Stewart et al., *Solid Phase Peptide Synthesis*, 2*nd ed*. Pierce Chem. Co., Rockford, Ill. (1984)).

Mutated IL13 can also be produced through recombinant expression of IL13 encoding nucleic acids in which the nucleic acid is modified, randomly or in a site-specific manner, to change (substitute), add to, or delete, some or all of the amino acids in the encoded polypeptide. Alanine-scanning mutagenesis is widely used to examine structure function relationships of polypeptides.

Site-specific mutations canbe introduced into the IL13-encoding nucleic acid by a variety of conventional techniques, well described in the scientific and patent literature. Illustrative examples include: site-directed mutagenesis by overlap extension polymerase chain reaction (OE-PCR), as in Urban (1997) *Nucleic Acids Res*. 25: 2227–2228; Ke (1997) *Nucleic Acids Res*., 25: 3371–3372, and Chattopadhyay (1997) *Biotechniques* 22:1054–1056, describing PCR-based site-directed mutagenesis "megaprimer" method; Bohnsack (1997) *Mol. L Biotechnol*. 7: 181–188; Ailenberg (1997) *Biotechniques* 22: 624–626, describing site-directed mutagenesis using a PCR-based staggered re-annealing method without restriction enzymes; Nicolas (1997) *Biotechniques* 22: 430–434, site-directed mutagenesis using long primer-unique site elimination and exonuclease III. Unique-site elimination mutagenesis can also be used (see, e.g., Dang et al. (1992) *Anal. Biochem.*, 200: 81). The production of muteins of biologically active proteins such as IFN- beta and IL-2 is described in detail in U.S. Pat. No. 4,853,332 and the mutation of IL13 is described in Example 1.

Modified IL13 of this invention can be further produced by chemical modification methods, see, e.g., Belousov (1997) *Nucleic Acids Res.* 25:3440–3444; Frenkel (1995) *Free Radic. Biol. Med.* 19: 373–380; Blommers (1994) *Biochemistry* 33: 7886–7896, and the like.

ii) Screening the IL13 Muteins

The mutagenized IL13 molecules can then be screened to identify those that preferentially bind to the restrictive (IL4 receptor independent) IL13 receptor and show reduced or no interaction (e.g. binding with the IL13/IL4 receptor in general or specifically either the 140 kDa $hIL4_\beta$ subunit or the 70 kDA $IL13R\alpha^1$). It is possible to assay for simple binding (e.g., detecting the competition of mutagenized IL13 with binding of labeled wild-type IL13 to an IL13 or IL4 receptor), or, alternatively, to assay for some biological activity (e.g., the activity of an effector molecule) mediated through the binding of the mutagenized IL13 and/or the mutagenized IL13 chimeric molecule. A simple binding assay is described in U.S. Pat. No. 5,614,191.

The data generally suggest that IL13 receptor on gliomas (e.g. cell lines U-251 MG and SNB-19) is restricted in that it does not interact with IL4. Thus these cells provide a good target for assaying for positive IL13R binding or activity. Other cells such as HUVEC endothelial cells express an IL13/IL4 receptor that appears to utilize the common 140 kDa $hIL4_\beta$ subunit and contain the 70 kDa $IL13R\alpha^1$ subunit. These cells thus provide good targets for assaying reduced binding or activity of the mutagenized IL13 molecules. Thus preferred mutagenized IL13 molecules or chimeric molecules of this invention show increased activity on U-251 MG and SNB-19 glioma and similar cells and reduced binding or activity on HUVEC (endothelial) cells. This can be assayed in a proliferative assay (see, e.g., the proliferative assay on TF-1 cells that express the shared IL13/IL4 receptor described in Example 1).

In a particularly preferred embodiment, the mutagenized IL13 is expressed in fusion with a cytotoxin (e.g. PE38QQR, PE4E, etc.) and the cytotoxic activity (e.g. inhibition of growth or proliferation or uptake of labeled substrate such as amino acids, etc.) on the target cells is assayed. Methods of assaying such activity are well known to those of skill in the art and are illustrated, in Example 1 and in U.S. Pat. No. 5,614,191. Other suitable assays include the inhibition of RANTES induction by TNF and IFNγ (Farfaing-Koka et al., (1995) J. I. 154: 1870–1878).

It will be appreciated that such assays can be performed in single assay format. Alternatively, such assays are amenable to "parallel" processing in a high throughput screening system e.g., using a BiaCore system to assay binding (see, e.g., Nang et al. (1997) *Proc. Nat. Acad. Sci. USA*, 94:1654–1662).

High throughput assays for the presence, absence, or quantification of protein binding or cell activity are well known to those of skill in the art. Thus, for example, U.S. Pat. No. 5,559,410 discloses high throughput screening methods for proteins, while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass, etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

III. The Effector Molecule

As described above, the effector molecule component of the chimeric molecules of this invention may be any molecule whose activity it is desired to deliver to cells that overexpress IL13 receptors. Particularly preferred effector molecules include cytotoxins such as PE or DT, radionuclides, ligands such as growth factors, antibodies, detectable labels such as fluorescent or radioactive labels, and therapeutic compositions such as liposomes, lipids, and various drugs.

A) Cytotoxins.

Particularly preferred cytotoxins include Pseudomonas exotoxins, Diphtheria toxins, ricin, and abrin. Pseudomonas exotoxin and Diphtheria toxin are most preferred.

i) Pseudomonas Exotoxin (PE).

Pseudomonas exotoxin A (PE) is an extremely active monomeric protein (molecular weight 66 kD), secreted by Pseudomonas aeruginosa, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity (see Siegall et al. (1989) *J. Biol. Chem.* 264: 14256–142610.

Where the mutagenized IL13 is fused to PE, a preferred PE molecule is one in which domain Ia (amino acids 1 through 252) is deleted and amino acids 365 to 380 have been deleted from domain lb. However all of domain Ib and a portion of domain II (amino acids 350 to 394) can be deleted, particularly if the deleted sequences are replaced with a linking peptide.

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, sequences that function to maintain or recycle proteins into the endoplasmic reticulum, referred to here as "endoplasmic retention sequences". See, for example, Chaudhary et al, *Proc. Natl. Acad. Sci. USA* 87: 308–312 and Seetharam et al (1991) *J. Biol. Chem.* 266: 17376–17381.

Deletions of amino acids 365–380 of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial.

In a preferred embodiment, the mutagenized IL13 targeting molecule is inserted in replacement for domain Ia Preparation of an analogous molecule, IL13-PE38QQR, is described in U.S. Pat. No: 5,614,191. In addition, similar insertions have been accomplished in what is known as the TGFα-PE40 molecule (also referred to as TP40) described in Heimbrook et al. (1990) *Proc. Natl. Acad. Sci, USA*, 87: 4697–4701 and in U.S. Pat. No. 5,458,878.

Preferred forms of PE contain amino acids 253–364 and 381–608, and are followed by the native sequence or mutant sequences described in Chaudhary et al.(1990), *Proc. Nat. Acad Sci. USA* 87: 308–312. Lysines at positions 590 and 606 may or may not be mutated to glutamine.

In a particularly preferred embodiment, the IL13 receptor targeted cytotoxins of this invention comprise the PE molecule designated PE38QQR. This PE molecule is a truncated form of PE composed of amino acids 253–364 and 381–608. The lysine residues at positions 509 and 606 are replaced by glutamine and at 613 are replaced by arginine (Debinski et al. (1994) *Bioconj. Chem.*, 5: 40).

In another particularly preferred embodiment, the IL13 receptor targeted cytotoxins of this invention comprise the PE molecule designated PE4E. PE4E is a "full length" PE with a mutated and inactive native binding domain where amino acids 57, 246, 247, and 249 are all replaced by glutamates (see, e.g., Chaudhary et al. (1995) *J. Biol. Chem.*, 265: 16306).

The mutagenized IL13 targeting molecule may also be inserted at a point within domain III of the PE molecule. In this instance, the mutagenized IL13 molecule is preferably fused between about amino acid positions 607 and 609 of the PE molecule. This means that the mutagenized IL13 is inserted after about amino acid 607 of the molecule and an appropriate carboxyl end of PE is recreated by placing amino acids about 604–613 of PE aaer the targeting molecule. Thus, the mutagenized IL13 is inserted within the recombinant PE molecule after about amino acid 607 and is followed by amino acids 604–613 of domain III. The mutagenized IL13 may also be inserted into domain Ib to replace sequences not necessary for toxicity. Debinski, et al. *Mol. Cell. Biol.*, 11: 1751–1753 (1991).

In a preferred embodiment, the PE molecules are fused to the targeting molecule by recombinant means. The genes encoding protein chains may be cloned in cDNA or in genomic form by any cloning procedure known to those skilled in the art (see, e.g., Sambrook et al. (1989), *Molecular Cloning: A Laboratory Manual*, Cold Spring Harbor Laboratory). Methods of cloning genes encoding PE fused to various ligands are well known to lose of skill in the art (see, e.g., Siegall et al. (1989) *FASEB J.*, 3: 2647–2652; and Chaudhary et al. (1987) *Proc. Natl. Acad. Sci. USA*, 84: 4538–4542).

Those skilled in the art will realize that additional modifications, deletions, insertions and the like may be made to the chimeric molecules of the present invention or to the nucleic acid sequences encoding IL13 receptor-directed chimeric molecules. Especially, deletions or changes may be made in PE or in a linker connecting the mutagenized IL13 to PE, in order to increase cytotoxicity of the fusion protein toward target cells or to decrease nonspecific cytotoxicity toward cells without antigen for the antibody. Such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

ii) Diphtheria Toxin (DT).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science*, 175: 901–903 (1972); Uchida et al. *J. Biol. Chem.*, 248: 3838–3844 (1973)).

In a preferred embodiment, the targeting molecule-Diphtheria toxin fusion proteins of this invention have the native receptor-binding domain removed by truncation of the Diphtheria toxin B chain. Particularly preferred is DT388, a DT in which the carboxyl terminal sequence beginning at residue 389 is removed. Chaudhary, et al. (1991) *Bioch. Biophys. Res. Comm.*, 180: 545–551.

Another preferred diphtheria toxin is DT390 a diphtheria toxin in which the native binding domain is eliminated and the L at position 390 is followed by SPGPVPPST of the mutagenized IL13.

Like the PE chimeric cytotoxins, the DT molecules may be chemically conjugated to the IL13 receptor targeting molecule, but, in a preferred embodiment, the targeting molecule will be fused to the Diphtheria toxin by recombinant means. The genes encoding protein chains may be cloned in cDNA or in genomic form by any cloning procedure known to those skilled in the art. Methods of cloning genes encoding DT fused to various ligands are also well known to those of skill in the art (see, e.g., Williams et al. *J Biol. Chem.* 265: 11885–11889 (1990)).

The term "Diphtheria toxin" (DT) as used herein refers to full length native DT or to a DT that has been modified. Modifications typically include removal of the targeting domain in the B chain and, more specifically, involve truncations of the carboxyl region of the B chain. A mutagenized binding domain may also be present.

iii) Other Toxins.

It will be appreciated that the chimeric molecules of this invention can include cytotoxins other than diphtheria toxin or Pseudomonas exotoxin. Many such cytotoxins are known to those of skill and include but are not limited to ricin, abrin, saporin, pokeweed viral protein for virtually any other toxin that is capable of being conjugated or fused to a polypeptide.

B) Detectable Labels.

Detectable labels attached to the mutagenized IL13 molecules of this invention can be used in diagnostic assays (e.g., in the detection of shed tumor cells overexpression the IL13 receptor) and/or in the in vivo localization of tumor cells. Detectable labels suitable for use as the effector molecule component of the chimeric molecules of this invention include any composition detectable by spectroscopic, photochemical, biochemical, immunochemical, electrical, optical or chemical means. Useful labels in the present invention include biotin/avidin, magnetic beads (e.g. Dynabeads™), fluorescent dyes (e.g., fluorescein isothiocyanate, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and calorimetric labels are detected by simply visualizing the colored label, and so forth.

C) Ligands.

As explained above, the effector molecule may also be a ligand or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the tumor cells overexpressing the IL13 receptor. Suitable antibodies and growth factors are known to those of skill in the art and include, but are not limited to, IL-2, IL-4, IL-6, IL-7, tumor necrosis factor (TNF), anti-Tac, TGFα, SEA, SEB, and the like.

D) Nucleic Acids

Nucleic acids can also be attached to the mutagenized IL13 molecules of this invention. In this context, the IL13 acts as a non-viral vector effectively delivering the nucleic acid to the target cell. The nucleic acids can be attached directly to the mutagenized IL13, or it can be attached through a linker or it can be complexed with or encapsulated in another moiety (e.g., a lipid, a liposome, a viral coat, and the like) that is attached to the mutagenized IL13. The nucleic acid can provide any of a number of effector functions. The nucleic acid can encode one or more proteins and thereby deliver a particular enzymatic activity, substrate and/or epitope to the cell. In this context, it is typically desirable to express the nucleic acid and the nucleic acid is preferably a component of an expression cassette. The expression cassette typically includes a promoter initiation and termination codons and is selected to optimize expression in the target cell. Methods of constructing suitable expression cassettes are well known to those of skill in the art (see, e.g., Sambrook et al. (1989), *Molecular Cloning: A Laboratory Manual*, Cold Spring Harbor Laboratory).

The nucleic acid may also have a particular activity in its own right. Thus the nucleic acid may be an anti-sense nucleic acid or a ribozyme selected in inhibit the expression of one or more target genes.

E) Sensitizing Agents.

Other effector molecules include sensitizing agents that render the target (e.g., tumor) cell susceptible to various cancer therapeutics. The sensitizing agent can be a drug or a gene (under the control of a promoter in an appropriate expression cassette to induce expression in the target cell).

It has long been proposed that genes with a drug-conditional "killing" function be employed for treating tumors. For example, it has been proposed that expression of the herpes simplex virus (HSV) thymidine kinase (TK) gene in proliferating cells, renders the cells sensitive to the deoxynucleoside analog, ganciclovir (Moolten et at. (1986) *Cancer Res.* 46:5276–5281; Moolten et al. (1990) *Hum. Gene Ther.* 1: 125–134; Moolten et al. (1990) *J. Natl. Caucer Inst.* 82: 297–300; Short et al. (1990) *J. Neurosci Res.* 27: 427–433; Ezzedine et al. (1991) *New Biol.* 3: 608–614, Boviatsis et al. (1994) *Hum. Gene Ther* . 5: 183–191). HSV-TK mediates the phosphorylation of ganciclovir, which is incorporated into DNA strands during DNA replication (S-phase) in the cell cycle, leading to chain termination and cell death (Elion (1983) *Antimicr. Chemother.* 12, sup. B:9–17).

A second example of a gene with a drug-conditional "killing" function is the bacterial cytosine deaminase gene, which confers chemosensitivity to the relatively non-toxic 5-fluorouracil precursor 5-fluorocytosine (Mullen et al. (1992) *Proc. Natl. Acad. Sci USA* 89: 33–37; Huber et al. (1993) *Cancer Res.* 53: 4619–4626; Mullen et al. (1994) *Carcer Res.* 54: 1503–1506).

Still another example of a gene with a drug-conditional "killing" function is a cytochrome P450 gene. Expression, of the gene product renders tumor cells sensitive to a chemotherapeutic agent, in particular, cyclophosphamide or ifosphamide (see, U.S. Pat. No. 5,688,773).

Other sensitizing agents need not be genes. Thus, for example, U.S. Pat. No. 4,282,233 describes compounds that treat multiple drug resistance of susceptible tumor cells. Use of the chimeric molecules of this invention to deliver such compounds specifically to a tumor can reduce multiple drug resistance of the target cells rendering them susceptible to conventional cancer therapeutics.

F) Other Effector Moieties.

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxorubicin, vinblastine, genistein, an antisense molecule, and the like.

Alternatively, the effector molecule may be an encapsulation system, such as a liposome or micelle that contains a therapeutic composition such as a drug, a nucleic acid (e.g. an antisense nucleic acid), or another-therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.*, 28: 341–365 (1985)

IV. Attachment of the Targeting Molecule to the Effector Molecule

One of skill will appreciate that the targeting molecule, mutagenized IL13, and effector molecule(s) may be joined together in any order. Thus, the effector molecule may be joined to either the amino or carboxy termini of the mutagenized IL13. The mutagenized IL13 may also be joined to an internal region of the effector molecule, or conversely, the effector molecule may be joined to an internal location of the mutagenized IL13, as long as the attachment does not interfere with the respective activities of the molecules.

The mutagenized IL13 and the effector molecule may be attached by any of a number of means well known to those of skill in the art. Typically the effector molecule is conjugated, either directly or through a linker (spacer), to the mutagenized IL13. However, where the effector molecule is also a polypeptide it is preferable to recombinantly express the chimeric molecule as a single-chain fuision protein.

A) Conjugation of the Effector Molecule to the Mutagenized IL13.

In one embodiment, the targeting molecule (e.g., mutagenized IL13 or circularly permuted mutagenized IL13) is chemically conjugated to the effector molecule (e.g., a cytotoxin, a label, a ligand, or a drug or liposome). Means of chemically conjugating molecules are well known to those of skill.

The procedure for attaching an agent (effector) to an IL13 will vary according to the chemical structure of the agent.

Mutagenized IL13, like other polypeptides, contains variety of functional groups; e.g., carboxylic acid (COOH) or free amine ($-NH_2$) groups, which are available for reaction with a suitable functional group on an effector molecule to bind the effector thereto.

Alternatively, the mutagenized IL13 and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule (mutagenized IL13) to the effector molecule. The linker is capable of forming covalent bonds to both the mutagenized IL13 and to the effector molecule. Suitable linkers are well known to those of skill in the art and include, but are not limited to, straight or branched-chain carbon linkers, heterocyclic carbon linkers, or peptide linkers. Where the effector molecule is a polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired conjugate. Alternatively, derivatization may involve chemical treatment of the mutagenized IL13. For example, procedures for generation of free sulffiydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins (e.g., to antibodies) are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res*. 47: 4071–4075 (1987). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann (1991) *Science*, 252: 1657, U.S. Pat. Nos. 4,545,985 and 4,894,443.

In some circumstances, it is desirable to free the effector molecule from the mutagenized IL13 when the chimeric molecule has reached its target site. Therefore, chimeric conjugates comprising linkages which are cleavable in the vicinity of the target site may be used when the effector is to be released at the target site. Cleaving of the linkage to release the agent from the mutagenized IL13 may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

B) Production of Mutagnized IL13 Fusion Proteins.

Where the effector molecule is a polypeptide, the chimeric mutagenized IL13-effector molecules can be prepared as fusion proteins. The fusion proteins can be chemically synthesized as described above for mutagenized IL13.

However, in a preferred embodiment, the chimeric fusion proteins of the present invention are synthesized using recombinant DNA methodology. Generally this involves creating a DNA sequence that encodes the fuision protein, placing the DNA in an expression cassette under the control of a particular promoter, expressing the protein in a host, isolating the expressed protein and, if required, renaturing the protein.

DNA encoding the fuision proteins (e.g. IL13.E13K-PE38QQR) of this invention may be prepared by any suitable method, including, for example, cloning and restriction of appropriate sequences or direct chemical synthesis by methods such as the phosphotriester method of Narang et al. (1979) *Meth. Enzymol*. 68: 90–99; the phosphodiester method of Brown et al. (1979) *Meth. Enzymol*. 68: 109–151; the diethylphosphoramidite method of Beaucage et al. (1981) *Tetra. Lett*., 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention may be cloned using DNA amplification methods such as polymerase chain reaction (PCR). Thus, in a preferred embodiment, the gene for IL13 is PCR amplified, using primers that introduce one or more mutations. The primers preferably include restrictions sites, e.g., a sense primer containing the restriction site for NdeI and an antisense primer containing the restriction site for HindIII. In a particularly preferred embodiment, the primers are selected to amplify the nucleic acid starting at position 19, as described by McKenzie et al. (1987), supra. This produces a nucleic acid encoding the mature IL13 sequence and having terminal restriction sites. A PE38QQR fragment may be cut out of the plasmid pWDMH4–38QQR or plasmid pSGC242FdN1 described by Debinski et al. *Int. J Cancer*, 58: 744–748 (1994), and by Debinski et al. (1994) *Clin. Cancer Res*., 1: 1015–1022 respectively. Ligation of the mutagenized IL13 and a Pseudomonas exotoxin (e.g., PE38QQR) sequences and insertion into a vector produces a vector encoding the mutagenized IL13 joined to the terminus of the Pseudomonas exotoxin (e.g., joined to the amino terminus of PE38QQR or PEE (position 253 of the PE)). In a preferred embodiment, the two molecules are joined directly. Alternatively there can be an intervening peptide linker (e.g.,. a three amino acid junction consisting of glutamic acid, alanine, and phenylalanine introduced by the restriction site).

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the solubility, folding, net charge, or hydrophobicity.

The nucleic acid sequences encoding the fusion proteins may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride, or heat shock, transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology VoL.* 182: *Guide to Protein Punification.*, Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the IL13 receptor targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) *Bioconjug. Chem.*, 4: 581–585; and Buchner, et al. (1992) *Anal. Biochem.*, 205: 263–270). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the IL13 receptor targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

V. Identificatlon of Target Cells

The mutagenized IL13 molecules of this invention are particularly well suited as targeting moieties for binding tumor cells because tumor cells, overexpress IL13 receptors. In particular, carcinoma tumor cells (e.g. renal carcinoma cells) overexpress IL13 receptors at levels ranging from about 2100 sites/cell to greater than 150,000 sites per cell. Similarly, gliomas and Kaposi's sarcoma also overexpress IL13 receptors (IL13R). Moreover, substantially every cancer type tested to date appears to overexpress IL13 receptors as compared to the corresponding "healthy" tissue. Thus it appears that IL13 receptor overexpression is general characteristic of a neoplastic cells.

Thus, the methods of this invention can be used to target an effector molecule to virtually any neoplastic cell. Neoplasias are well known to those of skill in the art and include, but are not limited to, cancers of the skin (e.g., basal or squarnous cell carcinoma, melanoma, Kaposi's sarcoma, etc.), cancers of the reproductive system (e.g., testicular, ovarian, cervical), cancers of the gastrointestinal tract (e.g., stomach, small intestine, large intestine, colorectal, etc.), cancers of the mouth and throat (e.g. esophageal, larynx, oropharynx, nasopharynx, oral, etc.), cancers of the head and neck, bone cancers, breast cancers, liver cancers, prostate cancers (e.g., prostate carcinoma), thyroid cancers, heart cancers, retinal cancers (e.g., melanoma), kidney cancers, lung cancers (e.g., mesothelioma), pancreatic cancers, brain cancers (e.g. gliomas, medulloblastomas, meningiomas, etc.) and cancers of the lymph system (e.g. lymphoma).

In a particularly preferred embodiment, the methods of this invention are used to target effector molecules to kidney cancers, to skin cancers (especially Kaposi's sarcoma), and to brain cancers (especially gliomas, and medulloblastomas).

One of skill in the art will appreciate that identification and confirmation of IL13 overexpression by other cells requires only routine screening using well-known methods. Typically this involves providing a labeled molecule that specifically binds to the IL13 receptor (e.g., a native or mutagenized IL13). The cells in question are then contacted with this molecule and washed. Quantification of the amount of label remaining associated with the test cell provides a measure of the amount of IL13 receptor (IL13R) present on the surface of that cell. In a preferred embodiment, IL13 receptor may be quantified by measuring the binding of $^{125}$I-labeled IL13 ($^{125}$I-IL13) to the cell in question. Details of such a binding assay are provided in U.S. Pat. No. 5,614,191.

VI. Pharmaceutical Compositions

The mutagenized IL13 chimeric molecules (e.g., hIL13.E13K-PE4E and other cytotoxins) of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting compounds from digestion are well known in the art (see, e.g., U.S. Pat. No. 5,391,377 describing lipid compositions for oral delivery of therapeutic agents).

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g. buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Typically dosages will be adjusted to maximize dose while maintaining adverse effects at generally acceptable levels. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present chimeric molecules (e.g., fusion proteins), or a cocktail thereof (i.e., with other proteins, e.g., TGFα-PE38QQR), can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fuision proteins of the present invention are included a variety of disease conditions caused by specific human cells that may be eliminated by the toxic action of the protein. One preferred application is the treatment of cancer (e.g., a glioma), such as by the use of an mutagenized IL13 ligand attached to a cytotoxin (e.g., PE or a PE derivative).

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, is constrained by the blood-brain barrier which resists the entry of macromolecules into the subarachnoid space.

One of skill in the art will appreciate that in these instances, the therapeutic compositions of this invention can be administered directly to the tumor site. Thus, for example, brain tumors (e.g., gliomas) can be treated by administering the therapeutic composition directly to the tumor site (e.g., through a surgically implanted catheter). Where the fluid delivery through the catheter is pressurized, small molecules (e.g. the therapeutic molecules of this invention) will typically infiltrate as much as two to three centimeters beyond the tumor margin.

Alternatively, the therapeutic composition can be placed at the target site in a slow release formulation (e.g., a thrombin-fibrinogen mixture). Such formulations can include, for example, a biocompatible sponge or other inert or resorbable matrix material impregnated with the therapeutic composition, slow dissolving time release capsules or microcapsules, and the like.

Typically the catheter, or catheters, or time release formulation will be placed at the tumor site as part of a surgical procedure. Thus, for example, where major tumor mass is surgically debulked, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

VII. Diagnostic Kits

In another embodiment, this invention provides for kits for the treatment of tumors or for the detection of cells overexpressing IL13 receptors. Kits will typically comprise a chimeric molecule of the present invention (e.g. mutagenized IL13-label, mutagenized IL13-cytotoxin, mutagenized IL13-ligand, etc.). In addition the kits will typically include instructional materials disclosing means of use of chimeric molecule (e.g. as a cytotoxin, for detection of tumor cells, to augment an immune response, etc.). The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti- mouse-HRP, or the like). The kits may additionally include buffers and other reagents routinely used for the practice of a particular method. Such kits and appropriate contents are well known to those of skill in the art.

EXAMPLES

The following examples are offered to illustrate, but not to limit the present invention.

Recently, we have demonstrated that the vast majority of brain cancers (gliomas) abundantly express a receptor (R) for interleukin 13 (IL13). In order to achieve even more specific targeting of the IL13R in gliomas, we have mutagenized human (h) IL13. The mutation was made to alter IL13 interaction with the shared functional IL13/IL4 normal tissue receptor, but not with the glioma-associated receptor.

In one embodiment this invention involved mutating glutamic acid at position 13 to lysine. This mutant, designated hIL13.E13K was fused it to derivatives of Pseudomonas exotoxin A (PE). As demonstrated in the following examples, the mutated IL13-based cytotoxins are less active on normal cells and less toxic in vivo, and are better anti-tumor agents when compared with the cytotoxins containing non-mutagenized hIL13. We conclude that hIL13 is amenable to engineering which leads to a more discriminate recognition of the hIL13R that is cancer-associated from the shared IL13/IL4 R of normal tissue.

Example 1

Creation of Mutagenized IL13 and IL13 Cytotoxins

Materials

Restriction endonucleases and DNA ligase were obtained from New England Biolabs (Beverly, Mass.), Bethesda Research Laboratories (BRL, Gaithersburg, Md.) and Boehringer Mannheim (Indianapolis, Ind.). Fast protein liquid chromatography (FPLC) columns and media wore purchased from Pharmacia (Piscataway, N.J.). Oligonucleotide primers were synthesized at Macromolecular Core Laboratory at the Penn State College of Medicine. PCR kit was from Perkin-Elmer Cetus (Norwalk, Conn.). MTS/PMS for cell titer 96 aqueous non-radioactive cell proliferation assay was purchased from Promega (Madison, Wis.).

Plasmids, Bacterial Strains and Cell Lines.

Plasmids carry a T7 bacteriophage late promoter, a T7 transcription terminator at the end of the open reading frame of the protein, a f1 origin of replication and a gene for ampicillin resistance (Debinski et al. (1992) *J. Clin. Invest.* 90: 405–411). The cDNA encoding sequence for hIL13 was PCR-cloned to produce hIL13-PE38QQR, hIL13-PE4E, and hIL13, as described previously (Debinski et al. (1995) *Clin. Cancer Res.* 1: 1253–1258; Debinski et al. (1996) *J. Biol. Chem.* 271: 22428–22433; Debinski et al. (1995) *J. Biol. Chem.* 270: 16775–16780). Recombinant proteins were expressed in *E. coli* BL21 (λDE3) under control of the T7 late promoter (Studier et al. (1986) *J. Mol. Biol.* 189: 113–130). Plasmids were amplified in *E. coli* (HB101 or DH5α high efficiency transformation) (BRL) and DNA was extracted using Qiagen kits (Chatsworth, Calif.).

Construction of Plasmids Encoding hIL13.E13K-cytotoxins

Human IL13 (hIL3) was PCR-amplified in its mature form from a phuIL13 template (Debinski et al. (1995) *J. Biol. Chem.* 270: 16775–16780). A mutation of glutamic acid to lysine at position 13 in human interleukin 13 was incorporated into the sense PCR primer (hIL13.E13K sense primer 5'-AGGAGATATACATATGTCCCCAGGCCCTG-TGCCTCCCTCTACAGCCCTCAGGAAGCTCATTGAG-GA-3', SEQ ID NO: 1). The antisense primer was 5'-GTCGTGGGTGGATCCTCAGTTGAACCGTCCCTC-GCGAA-3' (SEQ ID NO: 2).

New sites were introduced for two restriction endonucleases Nde I and Hind III at the 5'and 3'ends of the interleukin gene, respectively. The digested fragments were subcloned into the expression vectors digested with the appropriate enzymes. The plasmids were sequenced using an automated ABI PRISM™ 377 DNA Sequencer (Foster City, Calif.) in the College of Medicine Molecular Genetics Core Facility.

Expression and Purification of Recombinant Proteins

*E. coli* BL21 (λDE3) cells were transformed with plasmids of interest and cultured in Terrific broth (Gibco, BRL). The cytotoxins and interleukins were localized to the inclusion bodies. The procedure for the recombinant proteins isolation from the inclusion bodies was described previously (Debinski et al. (1993) *J. Biol. Chem.* 268: 14065–14070). After dialysis, the renatured proteins were purified on ion-exchange columns and by size exclusion chromatography on Sephacryl S-100HR (Pharmacia). Protein concentration was determined by the Bradford assay (Pierce "Plus", Rocklford, Ill.) using BSA as a standard.

The recombinant proteins were expressed and purified to a high level of homogeneity as determined by STS-polyacrylamide gel electrophoresis. Electrophoresis was performed using 15% reduced SDS polyacrylamide gel stained with Coomassie Blue. Sephacryl S-100 HR purified recombinant proteins were loaded at 6 μg/lane. hIL13/IL13.E13K, hIL13-PE38QQR/hIL13.E13K-PE38QQR, hIL13-PE4E/hIL13.EPE4E were 12-, 50-, and 78-kDa proteins, respectively.

Example 2

Activity of Mutagenized IL13 Chimeric Molecules

Methods

Protein Synthesis Inhibition Assay

The activities of cytotoxins were tested as follows: usually $5\times10^3$ cells per well were plated in a 96-well tissue culture plate in 150 μl of media. Various concentrations of cytotoxins were diluted in 0.1% BSA/PBS and 25 μl of each dilution was added to cells 18–24 h following cell plating. Cells were incubated at 37° C. for another 48 h. Then, the cytotoxicity was determined using a calorimetric MTS [3-(4,5-dimethylthiazol-2-yl )-5-(3-carboxymethoxyphenyl)-2-(4-sulfophenyl)-2H-tetrazolium, inner salt]/PMS (phenazine methasulfate) cell proliferation assay. MTS/PMS was added at a half final concentration as recommended by the manufacturer. The cells were incubated with the dye for 4 hr and then the absorbance was measured at 490 nnm for each well using a micro-plate reader (Cambridge Technology, Inc., Watertown, Mass.). The wells containing cells treated with cycloheximide (10 mM) or wells with no viable cells left served as a background for the assay. We have used the same solutions of the cytotoxins for concomitant studies on normal and cancer cells. For blocking studies, interleukins at a concentration of 1.0 μg/ml were added to cells for 60 min before the cytotoxins addition. The results are expressed as $IC_{50}$ which is a concentration at which the cytotoxin inhibits the protein synthesis by 50%.

Cell Proliferation Studies

Cell proliferation studies using TF-1 cells were performed essentially as described (Zurawski et al. (1993) *EMBO J.* 12: 2663–2670). Maximal proliferative activities of the interleukins were obtained at a concentration of 100 ng/ml. The values were expressed as the difference between the background and maximal (recombinant proteins treated cells) MTS conversion that was recorded at $A_{490}$ nm. Data were obtained from the average of quadruplicates and the assays were repeated at least four times.

Binding Experiments of Recombinant Interleukins and their Cytotoxins to Human Glioma Cells 1 $\times10^6$ U-251 MG glioma cells was incubated with 100 μM $^{125}$I-hIL13 alone or in the presence of 0.1–500 nM unlabeled hIL13.E13K and hIL13 or hIL13.E13K-PE4E and hIL13-PE4E in duplicate tubes. The incubation was carried out at 4° C. for 4 hrs. The cultures were centrifuged (10,000 xg) through a phthalate oil mixture at 4° C. to separate cell-bound $^{125}$I-hIL13 from free $^{125}$I-hIL13. The cell pellet was cut off from each tube and radioactivity counted in a gamma counter. The experiment was done twice.

Anti-tumor Experiments

The U251-MG human malignant glioma cells ($6\times10^6$ per mouse) were implanted subcutaneously into female nu/nu athymic mice (4 to 5-wk old) on day 0. The treatment. started on day 11 or 12 when established tumors were formed. Cytotoxins were injected intratumorally as this route of drug delivery is envisioned for future clinical trials with hIL13-based cytotoxins (Wersall et al. (1997) *Cancer Immunol. Immunother*. 44: 157–164; Laske et al. (1997). *Nature Medicine* 3: 1362–1368). The injection volume was 25 $\mu$l and cytotoxins were diluted in PBS/0.1% BSA. Each treatment group was composed of five animals. Tumors were measured with a caliper and the formula for tumor volume calculation was as follows: length×width$^2$×0.4 (Debinski et al. (1993) *J. Biol. Chem*. 268: 14065–14070).

RESULTS hIL13.E13K Proliferative Activity is Altered

Figure 4:
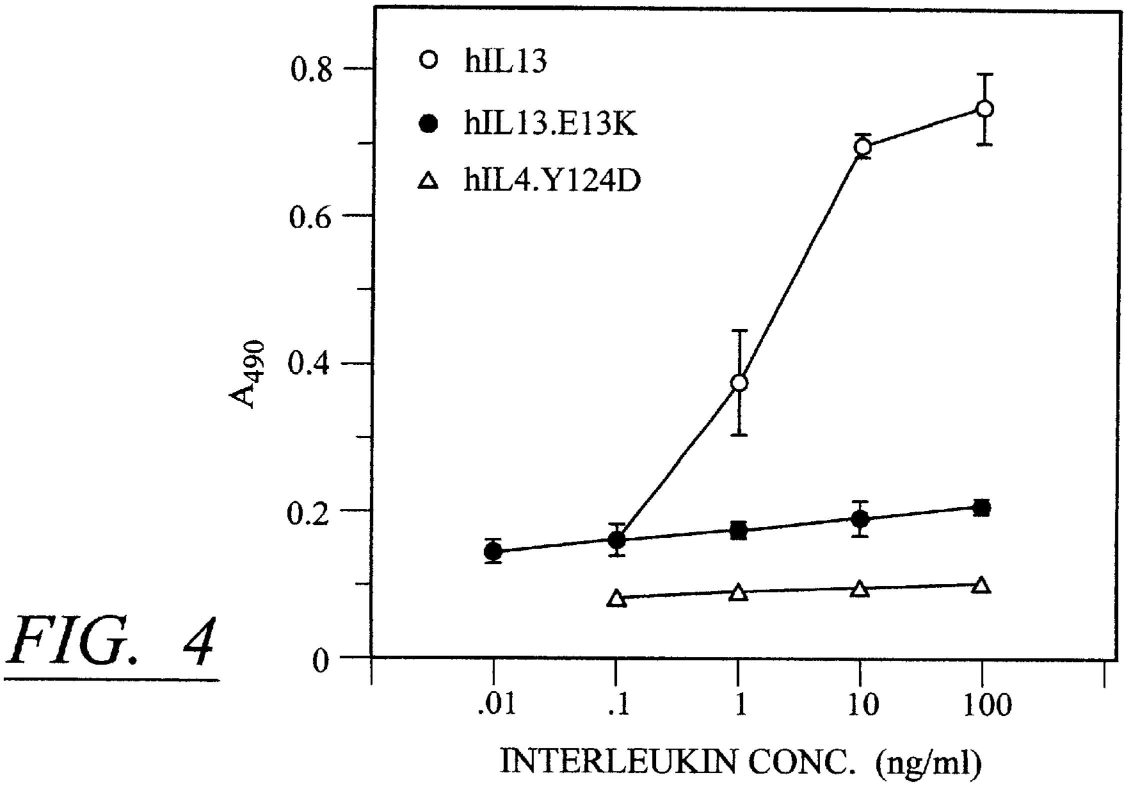
FIG. 4 illustrates the proliferative activities of hIL13, hIL13.E13K, and hIL4.Y124D on TF-1 cells. hIL4.Y124D was not used at a concentration of 0.01 ng/ml in these assays. The vertical bars represent SDs and may be smaller than the symbols.
Figure 5:
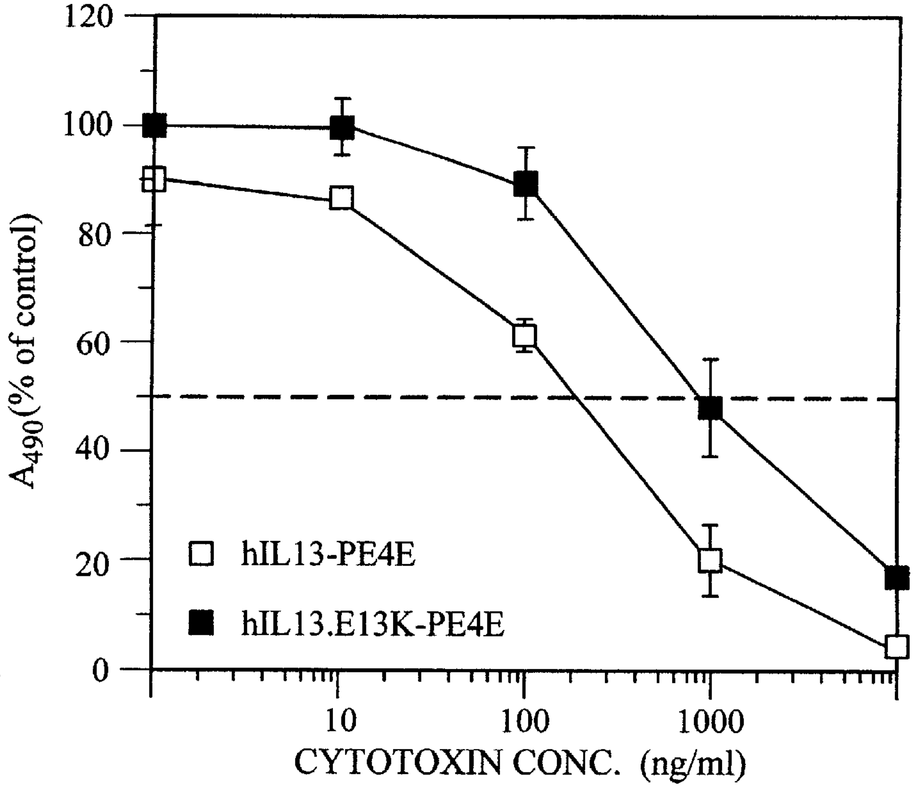
FIG. 5 illustrates the cytotoxic activity of hIL13-PE4E and hIL13.E13K-PE4E on HUVEC. The vertical bars represent SDs and may be smaller than the symbols.

We have measured proliferative responses to interleukins and their mutants in TF-1 cells (a human pre-myeloid erythrocytic leukemic cells which do express the shared IL13/4R) (Obiri et al. (1997) *J. Immunol*. 158: 756–764; Zurawski et al. (1993) *EMBO J*. 12: 2663–2670). We have treated TF-1 cells with hIL13, hIL13.E13K, and hIL4.Y124D (FIG. 4). hIL13 was very potent in stimulating the growth of TF-1 cells (FIG. 4). In contrast, hIL13.E13K was very weakly active, while hIL4.Y124D did not show any proliferative activity on its own on these cells.

hIL13.E13K Fused to a Bacterial Toxin is Less Active on Normal Human Cells than a Wild Type hIL13-containing Cytotoxin We next used normal human unbilical vein endothelial cells (HUVEC) which do express functional hIL13/4R as other selective normal tissues (Schnyder et al. (1996) *Blood* 87: 4286–4295, Bochner et al. (1995) *J. Immunol*. 154: 799–803, Sironi (1994) *Blood* 84: 1913–1921). We have found no $IC_{50}$ for hIL13-PE38QQR on these cells at up to 10,000 ng/ml concentration of the cytotoxin (Husain et al. (1997) *Clin. Cancer Res*. 3: 151–156). However, the more potent cytotoxin on cancer cells in vitro, hIL13-PE4E (Debinski et al. (1996) *J. Biol. Chem*. 271: 22428–22433), showed some killing activity on HUVEC ($IC_{50}$ of 200–400 ng/ml) (FIG. 5). When assayed side by side, hIL13.E13K-PE4E was five times less cytotoxic to HUVEC ($IC_{50}$ of~1000 ng/ml) than the cytotoxin containing a wild type hIL13. It is important to emphasize the need for high concentrations of the cytotoxins to evoke any effect on normal cells.

hIL13.E13K Cytotoxins Gain in a Potency on Human Glioma Cells

Figure 6A:
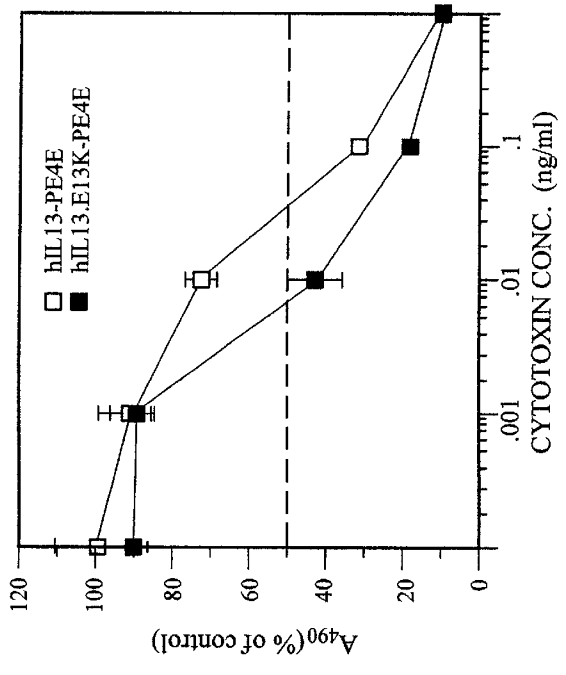
FIGS. 6A, 6B, and 6C illustrate the cytotoxic effect of hIL13.E13K-PE4E or hIL13-PE4E on SNB-19 cells (FIG. 6A) and U-251 MG cells (FIG. 6B). Neutralization of the cytotoxicity of hIL13.E13K-PE4E by hIL13, hIL13.E13K, and hIL4 on SNB-19 cells (FIG. 6C). hIL4 was not added to cells that were treated with the lowest concentration of the cytotoxin. The vertical bars represent SDs (A and B) and may be smaller than the symbols.
Figure 6B:
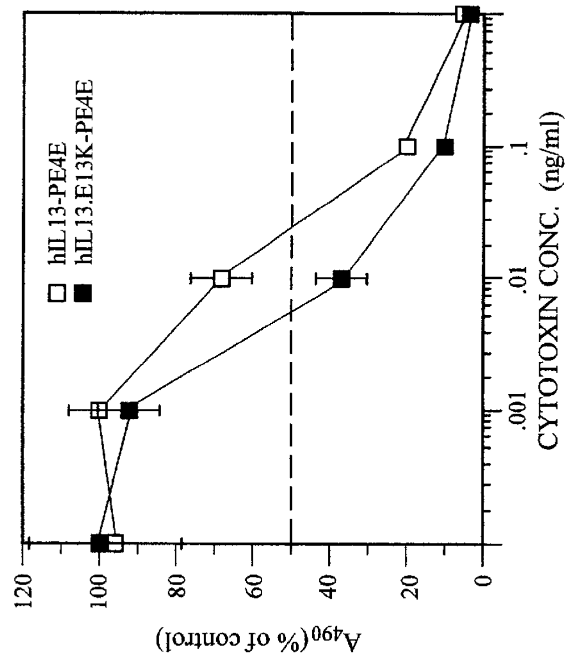
Figure 6C:
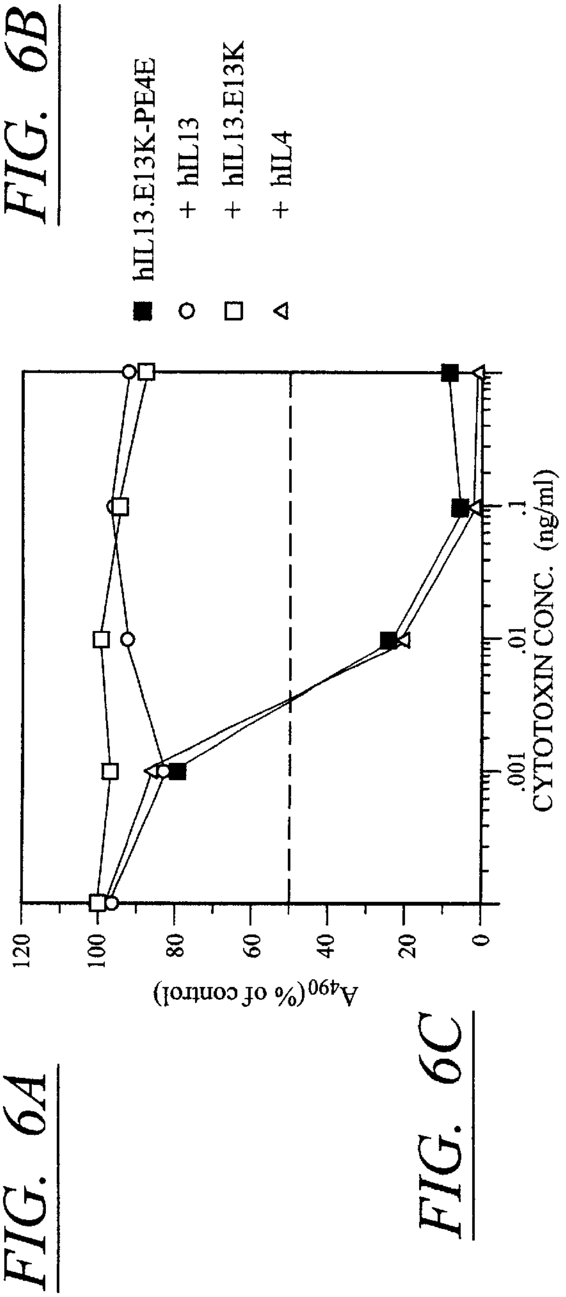

Since hIL13.E13K-PE4E showed a lesser cytotoxicity than hIL13-PE4E on normal cells (FIG. 5) it was possible that it may lose its potency on cancer cells as well. Thus, we treated several glioma cell lines with hIL13 cytotoxins. We have found that, e.g., SNB-19 glioma cells are extremely sensitive to hIL13.E13K-PE4E at an $IC_{50}$ as low as 0.7 pg/ml (FIG. 6A). On the other hand, although very potent, the cytotoxic action of hIL13-PE4E was surprisingly six times less than the one seen with the hIL13.E13K-PE4E (FIG. 6A). Similar gain in the cytotoxic potency ofhIL13.E13K-PE4E over hIL13-PE4E was observed on U-251 MG cells (FIG. 6B). On average, several other glioma cells were killed 3 to 10 times more potently with hIL13.E13K-PE4E than with hIL13-PE4E. These unanticipated results are in sharp contrast to a decrease in the cytotoxic activity of hIL13.E13K-PE4E on normal cells (FIG. 5).

hIL13 and hIL13.E13K. but not hIL4. Block the Action of hIL13.E13K Cytotoxins on Glioma Cells We also pretreated glioma cells with either hIL13 or hIL13.E13K before the addition of the cytotoxic fusion proteins. We found that the cytotoxic action of hIL13.E13K-PE4E is hIL13R-specific since it is blocked by an excess of hIL13 on all tested glioma cells (e.g., DBTRG MG in FIG. 6C). Moreover, hIL13.E13K neutralized the cytotoxicity of hIL13.E13K-PE4E similarly to hIL13. In contrast, but in accord with our previous studies (Debinski et al. (1995) *Clin. Cancer Res*. 1: 1253–1258; Debinski etal. (1996) *J. Biol. Chem*. 271: 22428–22433) hIL4 was ineffective in neutralizing the action of hIL13.E13K-PE4E (FIG. 6C).

Binding Avidity of Mutated hIL13 to Glioma Cells

Figure 7:
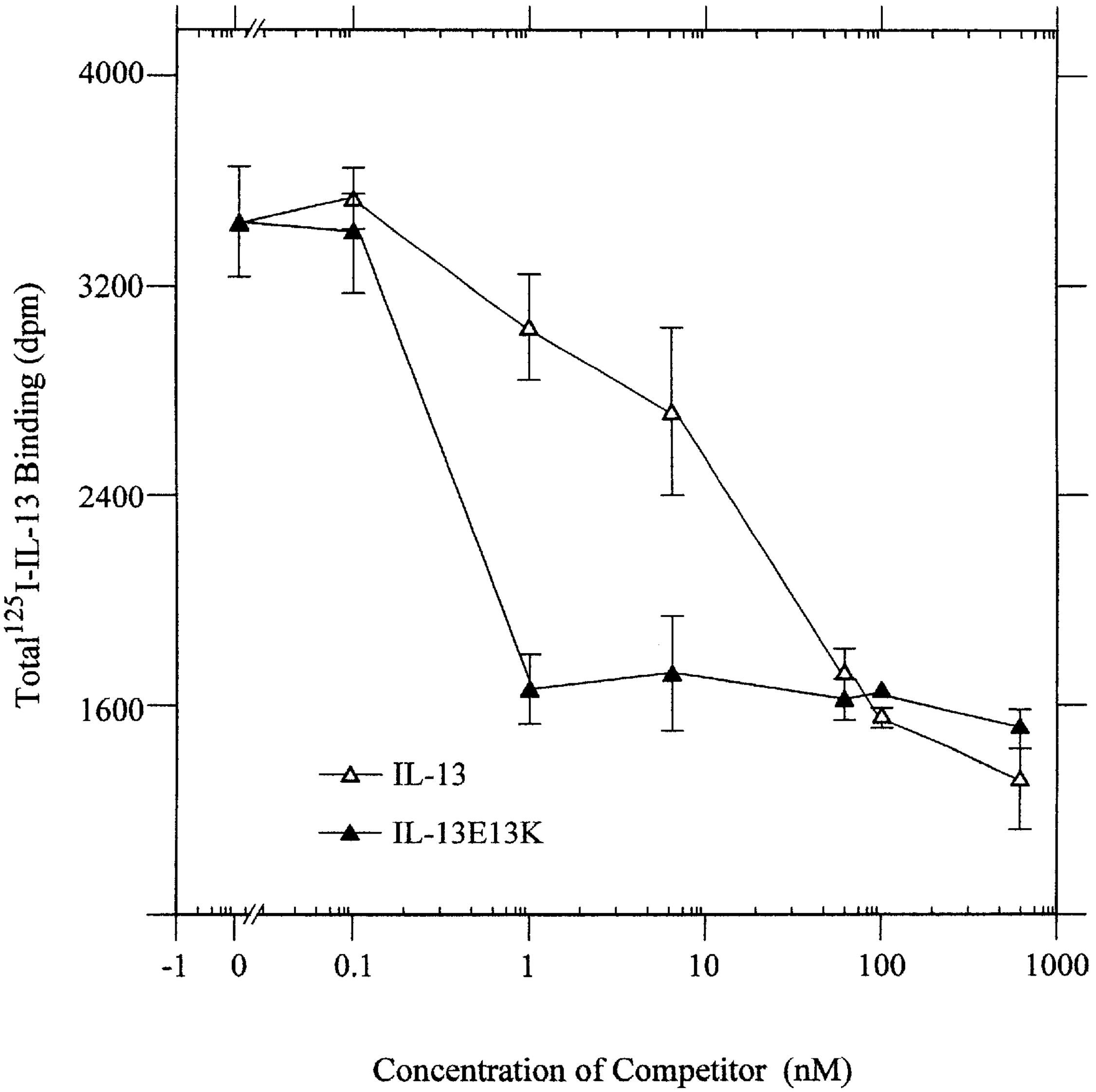
FIG. 7 illustrates competition for the binding sites for $^{125}$I-hIL13 by hIL13.E13K and hIL13 on U-251 MG cells.

To determine a possible reason for an unexpected enhanced potency of hIL13.E13K cytotoxins, the hIL13.E13K mutant and hIL13 were used in a competition assay for the binding sites for $^{125}$I-hIL13 on U-251 MG cells. The representative results are shown in FIG. 7. Both the mutated and wild type hIL13 competed efficiently for the radiolabeled hIL13 binding sites (FIG. 7). However, hIL13.E13K was approximately 50-fold better binding molecule than hIL13. Also hiL13.E13K-PE4E showed 8 to 10 times better affinity to glioma cells than hIL13-PE4E (data not shown).

Anti-tumor Activities of hIL3 Cytotoxins

Figure 8A:
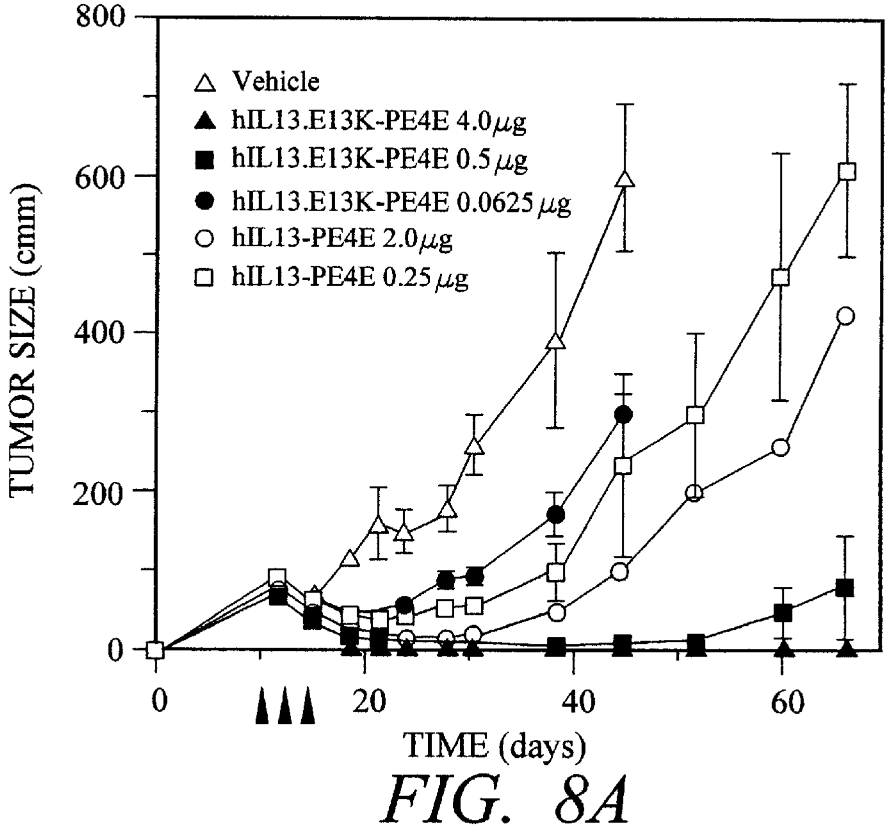
FIGS. 8A and 8B show the anti-tumor activities of hIL13.E13K and hIL13 cytotoxins on a human U251-MG glioma tumor growing in mice. The arrowheads indicate the days of cytotoxins injections. The vertical bars correspond to the SEs and may be smaller than the symbols (not shown for hIL13-PE4E 2.0 μg in 8A).

Since we have tested the interaction of cytotoxins containing mutagenized hIL13 with brain tumor cells in vitro (FIG. 6), it was important to compare their effects with that of wild type interleukin-containing cytotoxins in vivo. We have performed anti-tumor experiments in mice bearing the U-251 MG xenografis of human malignant glioma. IL13 is not species-specific therefore animal studies may closely reflect human situation. The treatment started on day 12 when tumors were formed and were larger than 50 mm$^3$ (FIG. 8A). Three injections of hIL13.E13K-PE4E every other day produced complete regressions in groups of mice receiving 4 $\mu$g and 0.5 $\mu$g per mouse of the cytotoxin, while 0.0625 $\mu$g of hIL13.E13K-PE4E per mouse evoked tumor growth inhibition. There were two deaths in the group receiving 4.0 $\mu$g of the cytotoxin but surviving mice remained free of tumor. Three out of five mice that received 0.5 $\mu$g of hIL13.E13K-PE4E per mouse were free of tumor on day 80. On the other hand, neither 2.0 $\mu$g per mouse nor 0.25 $\mu$g per mouse of hIL13-PE4E resulted in complete regressions in all treated mice, and there were 3 deaths in the former group of mice (FIG. 8A). Of interest, the tumor sites in the groups injected with hIL13.E13K-based cytotoxin appeared distinctively more inflammatory when compared with those in hIL13-PE4E-injected mice that even resulted in skin wounds. In a pilot experiment, we also found that six injections of 0.5 $\mu$g of hIL13.E13K-PE4E per mouse produced cures (100 days free of tumor) in all treated animals. The optimization of the treatment using hIL13.E13K cytotoxins is underway.

Figure 8B:
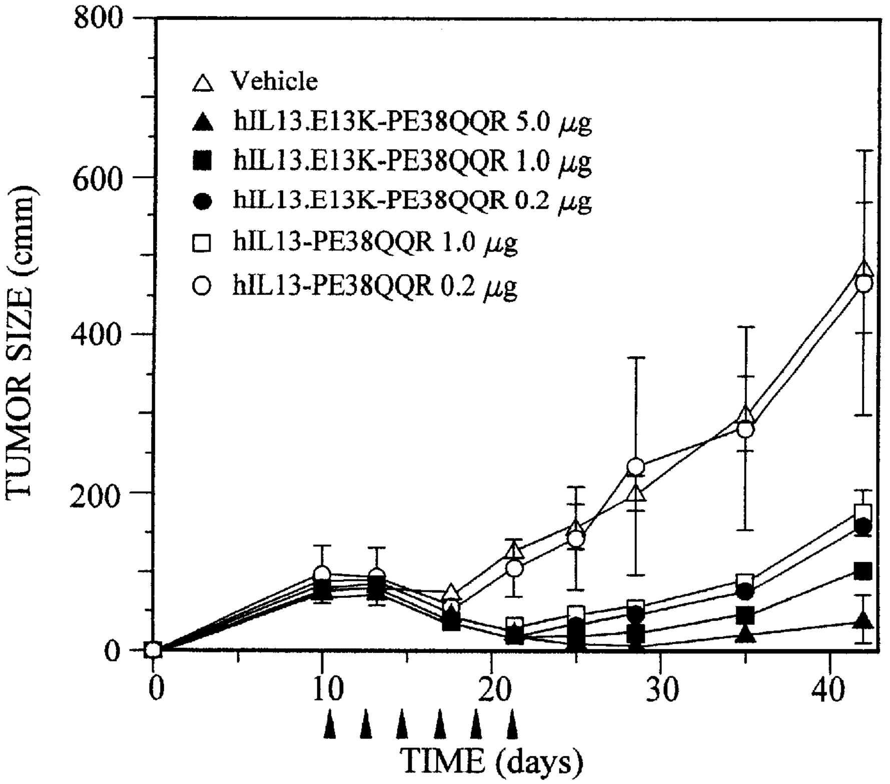

In a subsequent experiment, we used hIL13.E13K-PE388QQR and hIL13-PE388QQR which are less active than PE4E-containing cytotoxins on cancer cells in vitro (FIG. 8B). The mice bearing established U-251 MG tumors were treated with six injections of 5.0, 1.0, and 0.2 $\mu$g of either cytotoxin per mouse every other day (FIG. 8B). All mice treated with 5.0 $\mu$g of hIL13-PE38QQR per mouse were dead after the 4th injection while three out five mice survived this regimen in the hIL13.E13K-PE38QQR-treated group of animals (FIG. 8B). Tumors regressed in all mice treated with 1.0 $\mu$g of hIL13.E13K-PE38QQR per mouse while the same dose of hIL13-PE38QQR caused an arrest of tumors growth. Similarly, 0.2 $\mu$g of hIL13.E13K-PE38QQR per mouse produced much better anti-tumor effect than the corresponding dose of 0.2 $\mu$g of hIL13-PE38QQR per mouse (FIG. 8B). Again, the tumor sites in hIL13.E13K- based cytotoxin treated mice were visibly more inflammatory when compared with the hIL13-based cytotoxin treated mice, particularly at higher doses of the cytotoxins.

DISCUSSION

We have found that mutagenized hIL13, hIL13.E13K, in a cytotoxin is less toxic and exhibits better anti-tumor activity than the fusion.proteins based on the wild type interleukin. These data indicate an effective way to amplify therapeutic specificity of a tumor-associated receptor.

The functional normal tissue receptor for hIL13 interacts with hIL4 because it involves the 140-kDa hIL4R$_\beta$(Obiri et al. (1997) *J. Immunol.* 158: 756–764, Zurawski et al. (1993) *EMBO J.* 12: 2663–2670). The change in a conservative amino acid that has been implicated in the binding of hIL4 to the 140-kDa IL4R$_\beta$(Kruse et al. (1992) *EMBO J.* 12: 5121–5129) has caused alteration to the behavior of a mutagenized hIL13 as well. This further suggests that hIL13 is a structural homologue of hIL4. Furthermore, it is plausible that the interaction between hIL13 and the 140-kDa IL4R$_\beta$ is, at least in part, through a direct association of the hIL13 receptor binding region, located in its $\alpha$-helix A, with the extracellular domain of the 140-kDa IL4R$_\beta$. Further studies are underway to address these specific issues.

It is intriguing that the hIL13.E13K-containing cytotoxins are better anti-tumor agents while being less cytotoxic to normal cells and less toxic in vivo. It appears that hIL13.E13K may bind to glioma cells more avidly than the wild type interleukin and by this contributing to a better potency of cytotoxins. An increase in affinity may be a reflection of the shift in the binding of hIL13.E13K to a particular form(s) of the hIL13R that is present on cancer cells (Murata et al. (1997) *Biochem. Biophys. Res. Comm.* 238: 92–94). Also, we have observed differences in gross morphology of the tumor sites treated with hIL13.E13K-based cytotoxins. This is compatible with a more vigorous inflammatory infiltration into the region of dying cancer cells not being altered when hIL13.E13K cytotoxins are used, or, this phenomenon is related to a faster and more potent cancer cells killing.

The search for more active targeted cytotoxins has been directed at the improvement of their binding to the targeted receptor or better utilization of the pathways involved in the bacterial toxins' processing and/or intra-cytosolic delivery (Seetharam et al. (1991) *J. Biol. Chem.* 266: 17376–17381, Kreitman et al. (1994) *Proc. Natl. Acad. Sci.* 91: 6889–6893). These improvements affect normal cells as the cytotoxins become more toxic to them. Also, attempts at increasing efficacy of traditional anti-cancer drugs, chemotherapeutics, are linked to their more severe toxicities and more prominent mutagenicity (Chinnasamy et al. (1997) *Blood* 89: 1566–1573). Our approach, on the other hand, was first to decrease the already low interaction of cytotoxins with normal cells. We have identified a system in which this does not have to be paralleled by a decrease in the activity on brain tumor cells.

In sumnary, we have documented a unique single-reagent approach to increase the specificity of cytotoxins that are targeted to a glioma-associated receptor. This includes their diminished intracellular signaling on normal cells, an impaired targeting to normal cells, and an increased in anti-tumor activity on brain tumors.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A chimeric molecule having the formula:

$$R^1—(L)_j—(R^2)_n$$

wherein $R^1$ is a polypeptide comprising the amino acid sequence of SEQ ID NO:5;

j is 0 or 1;

n is at least 1;

$R^2$ is a cytotoxin; and

L is a linker.

2. The chimeric molecule of claim 1, wherein said cytotoxin is selected from a group consisting of PE4E and PE38QQR.

3. The chimeric molecule of claim 1, wherein said linker is a peptide linker.

4. The chimeric molecule of claim 1, wherein L or $R^2$, if present, are attached to the carboxyl terminus of $R^1$.

5. The chimeric molecule of claim 1, wherein L or $R^2$, if present, are attached to the amino terminus of $R^1$.

6. A method of delivering an effector molecule to a cell bearing an interleukin 13 receptor (IL13R), said method comprising the step of contacting said cell with a chimeric molecule comprising said effector molecule attached to a polypeptide comprising the amino acid sequence of SEQ ID NO:5.

7. The method of claim 6, wherein said effector molecule is a cytotoxin selected from a group consisting of PE4E and PE38QQR.

8. A method of inhibiting the growth of a cell expressing an IL13 receptor (IL13R), said method comprising contacting said cell with a cytotoxic molecule comprising a cytotoxin covalently attached to a polypeptide comprising the amino acid sequence of SEQ ID NO:5.

9. The method of claim 8, wherein said cytotoxin is selected from the group consisting of PE38QQR and PE4E.

10. The method of claim 8, wherein said cell is a neoplastic cell.

11. A pharmaceutical composition comprising a pharmacologically acceptable excipient; and a cytotoxic molecule comprising a cytotoxin covalently attached to a polypeptide comprising the amino acid sequence of SEQ ID NO:5.

12. The composition of claim 11, wherein said cytotoxin is selected from the group consisting of PE38QQR and PE4E.

* * * * *

UNITED STATES PATENT AND TRADEMARK OFFICE

CERTIFICATE OF CORRECTION

PATENT NO. : 6,296,843 B1
APPLICATION NO. : 09/054711
DATED : October 2, 2001
INVENTOR(S) : Debinski It is certified that error appears in the above-identified patent and that said Letters Patent is hereby corrected as shown below:

Column 1, line 4, prior to the heading "BACKGROUND OF THE INVENTION", insert the following heading and text:

STATEMENT REGARDING FEDERALLY SPONSORED RESEARCH OR DEVELOPMENT

This invention was made with support from the Government under Grant No. CA74145. The Government has certain rights in the invention.

Signed and Sealed this

Eighth Day of April, 2008

JON W. DUDAS
*Director of the United States Patent and Trademark Office*